US010357037B2

(12) United States Patent
Morris et al.

(10) Patent No.: US 10,357,037 B2
(45) Date of Patent: Jul. 23, 2019

(54) SYNTHESIS OF MOFS

(71) Applicant: University Court of The University of St Andrews, St Andrews (GB)

(72) Inventors: Russell Edward Morris, Fife (GB); Paul Stewart Wheatley, Fife (GB); Stewart Warrender, Fife (GB); Morven Duncan, Fife (GB)

(73) Assignee: University Court of the University of St Andrews, St Andrews (GB)

( * ) Notice: Subject to any disclaimer, the term of this patent is extended or adjusted under 35 U.S.C. 154(b) by 0 days.

(21) Appl. No.: 15/708,080

(22) Filed: Sep. 18, 2017

(65) Prior Publication Data
US 2018/0077937 A1 Mar. 22, 2018

Related U.S. Application Data

(62) Division of application No. 14/406,746, filed as application No. PCT/GB2013/051520 on Jun. 10, 2013, now Pat. No. 9,763,452.

(30) Foreign Application Priority Data

Jun. 11, 2012 (GB) .................................. 1210225.7
Sep. 20, 2012 (GB) .................................. 1216782.1

(51) Int. Cl.
*A01N 55/02* (2006.01)
*C07F 15/04* (2006.01)
*C07F 1/10* (2006.01)
*C07F 3/06* (2006.01)
*A01N 59/16* (2006.01)
*C07F 1/00* (2006.01)
*C07C 51/41* (2006.01)
*A01N 25/34* (2006.01)
*A01N 37/40* (2006.01)
*C07C 65/05* (2006.01)

(52) U.S. Cl.
CPC .............. *A01N 55/02* (2013.01); *A01N 25/34* (2013.01); *A01N 37/40* (2013.01); *A01N 59/16* (2013.01); *C07C 51/418* (2013.01); *C07C 65/05* (2013.01); *C07F 1/005* (2013.01); *C07F 1/10* (2013.01); *C07F 3/06* (2013.01); *C07F 15/045* (2013.01); *A01N 2300/00* (2013.01)

(58) Field of Classification Search
CPC ......... A01N 25/34; A01N 37/40; A01N 55/02
See application file for complete search history.

(56) References Cited

U.S. PATENT DOCUMENTS

| 8,399,005 B2 | 3/2013 | Schoenfisch et al. |
| 2005/0154222 A1 | 7/2005 | Muller et al. |
| 2011/0277767 A1 | 11/2011 | Yaghi et al. |
| 2012/0040471 A1 | 2/2012 | Chen et al. |

FOREIGN PATENT DOCUMENTS

| CN | 102336774 A | 2/2012 |
| DE | 102009027821 A1 | 1/2010 |
| EP | 1716157 B1 | 8/2007 |
| WO | WO 2007/029902 A1 | 3/2007 |
| WO | WO 2007/094567 A1 | 8/2007 |
| WO | WO 2008/020218 A1 | 2/2008 |
| WO | WO 2013/186542 A1 | 12/2013 |

OTHER PUBLICATIONS

Ding (Inorganic Chemistry Communications, 2005, 8, 38-40).*
Yong (Thesis for the degree of Master of Science in Chemical Engineering; Mar. 5, 2012).*
Abbasi (Ultrasonic Sonochemistry; 19, 2012, 846-852; available online Dec. 10, 2011).*
Abbasi et al., "Dense coating of surface mounted CuBTC Metal-Organic Framework nanostructures on silk fibers, prepared by layer-by-layer method under ultrasound irradiation with antibacterial activity", Ultrason. Sonochem., vol. 19, No. 4, pp. 846-852 (2012).
Akhbari and Morsali, "Thermal, solution and structural studies of a 3D Ag(I) coordination polymer with various Ag—AG bonds, [Ag₃(μ-Hbtc)(μ-H₂btc)]n" J. Iran. Chem. Soc,, vol. 5, No. 1, pp. 48-56 (2008).
Allan et al., "Metal-organic frameworks for the storage and delivery of biologically active hydrogen sulfide", Dalton Trans., vol. 41, No. 14, pp. 4060-4066 (2012).
Bao et al., "Adsorption of ethane, ethylene, propane, and propylene on a magnesium-based metal-organic framework", Langmuir., vol. 27, No. 22, pp. 13554-13562 (2011).
Blanita et al., "Process for the synthesis of organic-metal structures using microwave activation", STN CA Caeser Accession No. 1759, AN No. 2012:1176992 CAPLUS, 1 page, (2012) *Abstract*.
Botas et al., "Effect of Zn/Co ratio in MOF-74 type materials containing exposed metal sites on their hydrogen adsorption behavior and on their band gap energy", Int. J. Hydrogen Energy, vol. 36, pp. 10834-10844 (2011).
Chen and Liu, et al., "Synthesis, structureand fluorescence of {[NaCu(BTU)(H2O)4]2H2O]n, a double-sheet coordination polymer with 2D network", Huaxue Xuebao, vol. 62, No, 23, pp. 2323-2328 (2004) *Abstract Only*.
Dietzel et al., "Hydrogen adsorption in a nickel based coordination polymer with open metal sites in the cylindrical cavities of the desolvated framework", Chem. Commun. (Camb)., No. 9, pp. 959-961 (2006).
Dietzel et al., "Structural changes and coordinatively unsaturated metal atoms on dehydration of honeycomb analogous microporous metal-org4-anic frameworks", Chemistry, vol. 14, No. 8, pp. 2389-2397 (2008).
Dietzel et al., "Structural changes and coordinatively unsaturated metal atoms on dehydration of honeycomb analogous microporousmetal organic frameworks", STN CA Caesar Accession No. 1815, AN No. 2008:507769 CAPLUS, 2 pages (2008) *Abstract*.
(Continued)

*Primary Examiner* — Pancham Bakshi
(74) *Attorney, Agent, or Firm* — McDermott Will & Emery LLP; Judy M. Mohr; Wen Li

(57) ABSTRACT

The present invention relates to the synthesis of a variety of metal organic frameworks (MOFs) using low temperature and solvents which are considered to be not particularly harmful to the environment. There is also provided novel MOFs which may be made by the desired processes.

6 Claims, 30 Drawing Sheets

(56) References Cited

OTHER PUBLICATIONS

Dietzel et al., "Base-induced formation of two magnesium metal-organic framework compounds with a bifunctional tetratopic ligand", Eur. J. Inorg, Chem., pp. 3624-3632 (2008).

Ding et al., "Hydrothermal synthesis of a novel three-dimensional complex with strong blue luminescent properties", Inorg. Chem. Comm., vol. 8, pp. 38-40 (2005).

Du et al., "A hierarchical supra-nanostructure of HKUST-1 featuring enhanced $H_2$ adsorption enthalpy and higher mesoporosity", Electronic supplementary material for CrystEngComm, 6 pages (2011).

Ghermani et al., "Covalently bonded infinite zigzag chain structure in a novel Zn(II) complex of 2,5-dihydroxy-1,6-benzenedicarboxylic acid", Polyhedron, vol. 26, pp. 2880-2884 (2007).

Holmes et al., "Honeycombs, herringbones and brick-walls; three-fold guest-dependent variation in copper trimesate complexes bearing sulfimide ligands", Dalton Trans., No. 21, pp. 3488-3494 (2004).

International Search Report from PCT Patent Application No. PCT/GB2013/051520 dated Oct. 2, 2013, application now published as International Publication No. WO2013/186542 on Dec. 19, 2013.

Lee et al., "Honeycombs, herringbones and brick-walls; three-fold guest-dependent variation in copper trimesate complexes bearing sulfimide ligands", Bull. Korean Chem. Soc., vol. 31, No. 6, pp. 1489-1495 (2010).

McKinlay et al., "Exceptional behavior over the whole adsorption-storage-delivery cycle for NO in porous metal organic frameworks", J. Am. Chem. Soc., vol. 130, No. 31, pp. 10440-10444 (2008).

Morris and Wheatley, "Gas storage in nanoporous materials", Angew. Chem. Int. Ed., vol. 47, No. 27, pp. 4966-4981 (2008).

Nijem et al., "Molecular hydrogen "pairing" interaction in a metal organic framework system with unsaturated metal centers (MOF-74)", J. Am. Chem. Soc., vol. 132, No. 42, pp. 14834-14848 (2010).

Rosi et al., "Rod packings and metal-organic frameworks constructed from rod-shaped secondary building units", J. Am. Chem. Soc., vol. 127, No. 5, pp. 1504-1518 (2005).

Sun et al., "A novel luminescent 3D polymer containing silver chains formed by ligand unsupported Ag—Ag interactions and organic spacers", J. Chem. Soc., Dalton Trans., pp. 291-292 (2002).

Tranchemontagne et al., "Room temperature synthesis of metal-organic frameworks: MOF-5, MOF-74, MOF-177, MOF-199, and IRMOF-0", Tetrahedron, vol. 64, pp. 8553-8557 (2008).

Yong, "Continuous synthesis of metal-organic frameworks under pressure", Thesis submitted to the Oregon State University, pp. 1-50, presented on Mar. 5, 2012.

\* cited by examiner

SYNTHESIS OF MOFS

CROSS REFERENCE TO RELATED APPLICATIONS

This application is a division of U.S. application Ser. No. 14/406,746, filed Dec. 9, 2014, now U.S. Pat. No. 9,763,452, which is a U.S. National Stage of International Patent Application No. PCT/GB2013/051520, filed Jun. 10, 2013, which claims the benefit of priority to GB Application Nos. 1216782.1 filed Sep. 20, 2012, and 1210225.7, filed Jun. 11, 2012, each of which is hereby incorporated by reference in its entirety.

FIELD OF INVENTION

The present invention relates to the synthesis of a variety of metal organic frameworks (MOFs) using low temperature and solvents which are considered to be not particularly harmful to the environment. There is also provided novel MOFs which may be made by the desired processes.

BACKGROUND TO THE INVENTION

Coordination polymers are a class of materials which are formed from extended chains, sheets or networks of metal ions interconnected by ligands.

Metal organic frameworks—MOFs—are a type of coordination polymer having extended three dimensional framework structures and show great promise in a wide range of applications including gas storage/release and bacteria/infection control.[1] There is particular interest in porous MOFs with accessible coordinatively unsaturated metal sites since these have been shown to greatly enhance the gas storage-release profile.[2] For example, such sites are found in the honeycomb-like structure of the CPO-27 family[3,4] (or MOF-74).[5] These frameworks are constructed from chains of edge-sharing metal-oxygen polyhedra (octahedra when hydrated, square pyramids when dehydrated) connected by 2,5-dihydroxyterephthalate units. The large one-dimensional hexagonal channels permit easy access to the coordinatively unsaturated sites upon activation (dehydration). Indeed, such materials possess excellent adsorption/release profiles for many harmful and biologically active gasses including NO, $H_2S$ and $CO_2$.[2,6,7] They also show useful antibacterial properties both in their pristine and NO-loaded forms.

Metal organic frameworks possessing porous three-dimensional structures (such as CPO-27) are commonly and traditionally made via solvothermal routes. These approaches have several drawbacks when considering large scale commercial synthesis, including:

1) Use of harmful and environmentally unattractive organic solvents
2) High temperatures and long reaction times resulting in high processing cost
3) Requirement for sealed and pressure-rated vessel For example, MOFs constructed from chains of edge-sharing metal-oxygen octahedra connected by 2,5-dihydroxyterephthalate units and possessing a honeycomb structure were first reported by Dietzel et al.[3] and Rosi et al.[5] Both authors used solvothermal techniques to prepare Zn-, Co- and Ni-containing analogues. For example, Dietzel et al. reported the synthesis of Zn-CPO-27 by mixing a solution of 2,5-dihydroxyterephthalic acid in THF with an aqueous solution of Zn nitrate and aqueous sodium hydroxide.[4] The resulting mixture was heated in a sealed autoclave at 110° C. for three days. A similar procedure (without sodium hydroxide) was also reported for the Co and Ni analogues.[3,4] Rosi et al. employed a similar technique but with DMF as solvent and with a small amount of propanol. Subsequently, the Mg and mixed metal Zn/Co analogues were synthesised in a similar fashion from solutions of the acid linker and metal sources in DMF/water/ethanol and DMF/water solutions, respectively.[8,9]

Tranchemontagne et al.[10] reported that various MOFs, including Zn-CPO-27, can be made at room temperature and ambient pressure by mixing solutions of the relevant linker and metal source. In one example, MOF-5 (constructed from $Zn_4O$ units connected by 1,4-benzenedicarboxylate struts) was prepared by mixing solutions of the linker and Zn acetate in DMF at room temperate and in the presence of triethylamine. Although the amine was added to aid deprotonation of the linker, subsequent studies showed that it was not essential when using Zn. Zn-CPO-27 was synthesised in this way by replacing 1,4-benzenedicarboxylate with 2,5-dihydroxyterephthalic acid (DHTP). While this work removes the requirement for high temperature and pressurised vessels, it should be noted that the syntheses still rely on the use of the environmentally undesirable and hazardous organic solvent DMF.

Similarly, Rosi et al reported the synthesis of Zn-based MOF-69A and -69B at room temperature by dissolving Zn nitrate and linker in $DMF/H_2O_2$ with $CH_3NH_2$.[5]

The Cu-containing MOF HKUST-1 has been shown to form at room temperature either by mixing Cu acetate, 1,3,5-benzenetricarboxylic acid (BTC) and triethylamine in a 1:1:1 mixture of $DMF/EtOH/H_2O$, or by adding a solution of BTC in EtOH to a solution of Cu acetate in $H_2O$/acetic acid.[11]

The requirement to use organic solvents in conventional syntheses is dictated by the solubility of the acid linker. For example, 2,5-dihydroxyterephthalic acid is insoluble in water but dissolves in solvents such as THF and trimesic acid is only slightly soluble in water.

A coordination polymer formed between Zn and DHTP but with a different structure to CPO-27 was synthesised by Ghermani et al. at room temperature.[12] The material was prepared by adding an aqueous solution of Zn sulphate to the neutralised linker in aqueous sodium hydroxide. However, the resulting structure is composed of linear chains and is non-porous. It is therefore not expected to possess significant gas adsorption capacity.

Akhbari, K. and Morsali, A. J. Iran. Chem. Soc., 2008, 5(1), 48-56 describe the structure and physical characteristics of a Ag(I) trimesate coordination polymer, which is thought to be composed of linear chains. Although it is synthesised at room temperature, the process depends on the use of flammable and toxic methanol. An alternative method of preparation of this material is described by Sun, D., Cao, R., Weng, J., Hong, M. and Liang, Y., J. Chem. Soc., Dalton Trans., 2002, 291-292. The method is a small scale and lengthy lab process not conducive to industrial application.

Methods of synthesising silver MOFs require either high temperatures and pressures (for example, Ding, B., Yi, L., Liu, Y., Cheng, P., Dong, Y-B. and Ma, J-P., Inorg. Chem. Comm., 8, 2005, 38-40) or low temperatures and use of organic solvents (for example, WO 2007/094567 and WO 2007/029902 of Yeong et al.).

It is an object of the present invention to provide a method of MOF synthesis which obviates and/or mitigates one or more of the aforementioned disadvantages.

SUMMARY OF THE INVENTION

According to a first aspect, the present invention provides a method of synthesising a MOF of the form of $M_x(L)_y(OH)_v(H_2O)_w$ wherein;

M is a metal or metals
L is a benzene polycarboxylate linker; and
x is 1-10, y is 0.1-3, v is 0-2 and w is 0-14;

the method comprising the step of providing a salt of L or an aqueous solution thereof; and mixing this with a solution of a metal salt/source at a temperature between 0° C. and 100° C., in order to obtain said MOF.

In some embodiments, x is 2-10, y is 0.8-1.2, v is 0-1 and w is 0-14.

In some embodiments, x is 2-4.

One or more of the water molecules may be present as ligands and form part of the three dimensional network structure of the MOF. One or more of the water molecules may be present as hydrating water molecules and be bound to the network structure.

As will be understood by a skilled reader, one or more water molecules may be disassociated, for example so as to form a protanated "$H_3O^+$" species and a coordinating $OH^-$ ligand, together with a further water molecule.

The total amount of water w of the MOF may vary depending on the degree of hydration.

Hydroxide ligands may form part of the framework structure, and may be coordinated to more than one metal ion within the framework structure.

The method may comprise providing a water soluble salt of L, in particular of DHTP. The metal salt/source may be dissolved in water or may be dissolved in a water/co-solvent mixture.

By benzene polycarboxylate linker we mean a polydentate (for example di- or tridentate) linking ligand comprising a benzene ring and at least two carboxylate groups and, optionally, one or more further substituents to the benzene ring.

In some embodiments, L is a benzene dicarboxylate or a benzene tricarboxylate. L may be a dihydroxy benxene dicarboxylate, in particular 2,5-dihydroxyterphthalate (DHTP); i.e. In some embodiments, L is

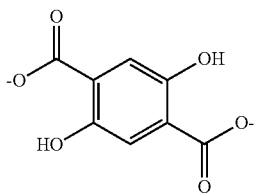

L may be 1,3,5-benzene tricarboxylate (BTC). i.e. In some embodiments, L is

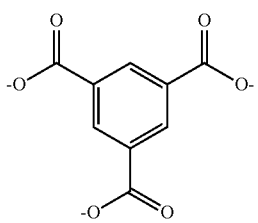

M may be any metal or metals, but preferably Zn, Ni, Mn, Mg, Ag, Cu, Na. M may comprise Ca, Co, Fe. In embodiments comprising BTC, M is preferably Ag.

The MOF may be of the form $M_2M'_z(DHTP)(H_2O)_2.qH_2O$; wherein q is 0-12, z=0-8; and M is one or metals selected from, and M' is a further metal selected from, the group Zn, Ni, Mn, Mg, Ag, Cu, Na.

The MOF may be of the form of $M_2(DHTP)(H_2O)_2.qH_2O$, where the number of hydrating water molecules q is 0-12.

The MOF may be of the form of $M_{x'}(BTC)_{y'}(OH)_{v'}(H_2O)_{w'}$, where x' is 1-5, y' is 0.1 to 3, v' is 0 to 2 and w' is 0-5.

x' may be in the range of 2-4, or 3-4. y' may be in the range from around 0.5 to 2, or 0.8 to 1.2.

The MOF may be of the form of $M_{x'}(BTC)_{y'}(OH)_{v'}(H_2O)_{w'}$, where x' is 3-4, y' is 0.8 to 1.2, v' is 0 to 1 and w' is 0-5.

M may be Ag.

One or more metal ions, in particular may form part of the framework structure, or may be present as charge balancing counter ions within pores or channels and bound to the framework structure.

In some embodiments, the method comprises providing the sodium salt of L, or alternatively the potassium or magnesium salt of L.

The salt of L may be water soluble (in water at or around pH 7) or may be soluble in aqueous conditions above a threshold pH, for example above approximately pH 6, pH 7 or in some embodiments above approximately pH 10. The salt of L may be water soluble at a pH of below 14, or below 12 or 10.

The method may comprise adding together a salt or a conjugate acid of L and a basic solution (and/or increasing the pH of water or an aqueous solution in contact with the salt or conjugate acid of L) so as to provide an aqueous solution having a sufficiently high pH to dissolve the salt of conjugate acid of L and thereby provide an aqueous solution of a salt of L.

The salt of L, or an aqueous solution thereof, may be synthesised in advance, or may be synthesised as part of the method.

The salt of L, or aqueous solution thereof, may be prepared by addition of a compound comprising L (for example a conjugate acid or a salt of L, such as 2,5-dihydroxyterephthalic acid or trimesic acid—1,3,5-benzene tricarboxylic acid) and a base. For example, a water soluble salt of DHTP may be prepared by addition of 2,5-dihydroxyterephthalic acid and sodium hydroxide, to produce a solution of the sodium salt of DHTP.

Typically, the method comprises adding the compound comprising L, or a solution or suspension of the compound comprising L, to a basic solution, e.g. sodium hydroxide solution, to thereby provide an aqueous solution of a salt of L.

In some embodiments, the method comprises inducing precipitation of the salt of L from the solution of L in aqueous sodium hydroxide, or another suitable base. Precipitation may be induced by addition of a solvent, such as ethanol, or by evaporation of water. In both cases the product can be purified by reflux in ethanol prior to further use. In one embodiment, the method comprises inducing precipitation of $Na_2DTHP$ from an aqueous sodium hydroxide, the solution comprising a molar ratio Na: DHTP preferably but not restricted to 1-6, such as 2-4.

In other embodiments, the method comprises adding together an aqueous suspension of an acid linker (e.g. trimesic acid), or an insoluble (or substantially insoluble) salt of L, and a basic solution. The solutions are preferably added together in amounts so as to achieve a pH above which the particles in the suspension dissolve, so as to form an aqueous solution of the salt of L. The resulting aqueous solution of the salt of L may then be added to the solution of a metal salt/source, or vice versa (i.e. the solutions may be added together in any order).

The basic solution may be any suitable basic solution, including for example an aqueous solution of sodium or potassium hydroxide, or an aqueous solution of an organic base such as ammonia, trimethylamine or triethylamine.

The MOF may be prepared by adding an aqueous solution of the salt of L to a solution of the metal salt/source, typically in water or water/co-solvent, under vigorous mixing such as brisk stirring, at the desired temperature and for a desired length of time.

Alternatively, the MOF may be prepared by adding a solution of the metal salt/source to an aqueous solution of the salt of L under vigorous mixing such as brisk stirring, at the desired temperature and for a desired length of time.

The aqueous solution of L may be prepared from the salt of L induced to be precipitated from the basic solution, e.g. aqueous sodium hydroxide solution. The precipitated salt of L may be further purified, for example by recrystallisation or by refluxing in a second solvent, e.g. ethanol or propanol.

Alternatively, the MOF is prepared by adding a water soluble salt of L, metal salt/source, water and, optionally, co-solvent together directly into one vessel, and the mixture is vigorously mixed, e.g. stirred briskly, at the desired temperature and for a desired length of time.

A water soluble salt of L, or an aqueous solution of L, may be made in-situ.

For example an acid linker (a conjugate acid of L, for example 2,5-dihydroxyterephthalic acid) may be dissolved in aqueous metal hydroxide (e.g. sodium hydroxide) and the resulting solution added to a solution of the metal salt/source, preferably in water and optionally a co-solvent mixture, or vice versa.

In the above "in-situ" processes each mixture may be mixed e.g. stirred, vigorous at the desired temperature for a desired length of time before the product is obtained.

The metal salt/source can be any soluble metal salt, mixture of metal salts or mixed metal salt, such as one or more nitrates, chlorides or acetates. In embodiments wherein L is DHTP, the metal salt/source is preferably an acetate, to avoid formation of impurities. Where L is BTC, the metal salt/source is preferably a nitrate and preferably a co-solvent is not used.

The metal may be any metal or metals, but preferably selected from one or more of Zn, Ni, Mn, Mg, Ag, Cu, Na.

The co-solvent can be any solvent such as any alcohol, THF, DMF, DMSO. It is preferred, however, that less toxic and environmentally dangerous solvents such as ethanol or isopropanol are employed. Following the step of mixing, the metal/linker ratio (i.e. M/L) and water/co-solvent molar ratio (where co-solvent is present) are preferred but not limited to be in the ranges M/L=1-15, or more preferably 1-5, and water/co-solvent=3-100, respectively. The water/co-solvent molar ratio may be in the range of water/co-solvent=5-100, or 9-100. The water/co-solvent ratio may be in the range of 3-80. It will be understood that the water/co-solvent ratio in the metal salt/source solution may, in some embodiments, be lower than 3. The temperature is preferably, but not restricted to be, between 10 and 80° C.; more preferably 15-65° C. and 20-55° C.

Preferably, the method does not comprise use of environmentally damaging or highly toxic organic solvents (i.e. the co-solvent or a solvent added to cause precipitation or to wash and purify a precipitate), such as THF, DMF or DMSO or other non-alcoholic solvents. Preferably the method does not comprise use of methanol (which is known to be of higher flammability and toxicity than, for example, ethanol). In some embodiments, the method does not comprise use of organic solvents.

The time is preferred, but not limited to be, up to 3 days; more preferably up to 1 day. or preferably 30 min-6 hr to achieve maximum yield. For example, in a method of synthesising MOFs of the form $M_2(DHTP)(H_2O)_2.qH_2O$, the time is preferably in the range 2-6 hr and in a method of synthesising MOFs of the form $M_{x'}(BTC)_{y'}(OH)_{v'}(H_2O)_{w'}$, the time is preferably in the range 30 min-1 hr, e.g. around 45 mins.

In all cases the product may be recovered by an appropriate means suitable for the resulting particle size (for example filtration or centrifugation), washed in a suitable solvent and dried.

The method may further comprise changing the hydration of the MOF, for example by heating or otherwise drying the MOF or by washing or otherwise hydrating the MOF.

It has been found that the method may be used to prepare MOFs which are not known to result from conventional synthetic methods.

Accordingly, the invention extends to an MOF is obtained or obtainable by one or more of said methods as described herein above, in particular an MOF of the formula $Zn_xNi_yNa_z(DHTP)(H_2O)_2.qH_2O$; where the values of x+y+z=2 or x+y=2 and z=0-8 and q=0-12, or an MOF of the form $M_{x'}(BTC)_{y'}(OH)_{v'}(H_2O)_{w'}$ where x' is 2-4, y' is 0.5 to 2, v' is 0 to 2 and w' is 0-5 or where x' is 3-4, y' is 0.8 to 1.2, v' is 0 to 1 and w' is 0-5.

In a second aspect of the invention there is provided a novel MOF of the formula $Zn_xNi_yNa_z(DHTP)(H_2O)_2.qH_2O$; where the values of x+y+z=2 or x+y=2 and z=0-8 and q=0-12.

It will be understood that in relation to a given MOF, the value of w, the number of molecules of water of hydration present in the unit cell, will vary depending on the degree of hydration of the MOF.

The above MOF is preferably obtained or is obtainable by one or more of said methods as described herein above.

The MOF, of the present invention may be used for a variety of applications, known in the art, for example, the MOFs may be used for gas storage and optional release. Such an application is described in detail in WO2008/020218, incorporated herein by reference, to which the skilled reader is directed.

In a third aspect of the invention, there is provided a MOF of the form $M_{x'}(BTC)_{y'}(OH)_{v'}(H_2O)_{w'}$ where x' is 1-5, y' is 0.1 to 5, v' is 0 to 2 and w' is 0-5. x' may be in the range of 2-4, or 3-4. y' may be in the range from around 0.5 to 2, or 0.8 to 1.2.

The MOF may be of the form $M_{x'}(BTC)_{y'}(OH)_{v'}(H_2O)_{w'}$ where x' is 3-4, y' is 0.8 to 1.2, v' is 0 to 1 and w' is 0-5.

In some embodiments, x' is 3-4, y' is 0.8 to 1.2, v' is 0 and z' is 1-5.

M is preferably Ag. The MOF of the third aspect comprises a particularly high proportion of M, i.e. the metal to linker M/BTC ratio.

The MOF is preferably obtained or obtainable by the method of the first aspect.

The MOF is preferably obtained or obtainable by adding together a suspension of trimesic acid and a basic solution (e.g. sodium hydroxide), to thereby provide an aqueous solution of a salt of BTC.

The MOF is preferably obtained or obtainable by mixing an aqueous solution of a salt of BTC with an aqueous solution of a metal salt/source, for example aqueous silver nitrate.

It has been found that the MOF so obtained has a higher M/BTC ratio than materials prepared by conventional synthetic methods. The higher metal (e.g. silver) content is proposed to be associated with antibacterial activity. Thus, the invention further extends to use of the MOF of the third aspect as an antibacterial agent and to an article comprising the MOF of the first aspect. The MOF of the third aspect may form part of a coating formulation, such as a paint or a powder coat comprising the MOF of the third aspect. The article may for example be a fabric (woven or non-woven) or a plastics material coated or impregnated with the MOF, or a formulation comprising the MOF. The formulation may further comprise surfactants, fixing agents and other additives known to the skilled reader.

The MOFs of the present invention may also be used in terms of antimicrobial actions and again this is described in detail and the MOFs may be modified as described in WO2012/020214, incorporated herein by reference, to which the skilled reader is directed.

The present invention will now be further described by way of example and with reference to figures which show:

DESCRIPTION OF THE DRAWINGS

The invention will now be described with reference to the following drawings in which:

FIG. 8 shows XRD patterns for $Zn_xNa_z(dhtp)(H_2O)_g \cdot hH_2O$ prepared (a) as per example 3b, (b) as per example 3a.

FIG. 9 shows XRD patterns for $Zn_xNa_z(dhtp)(H_2O)_g \cdot hH_2O$ prepared (a) as per example 3a, (b) as per example 11a.

DETAILED DESCRIPTION OF EXAMPLE EMBODIMENTS

Figure 1:
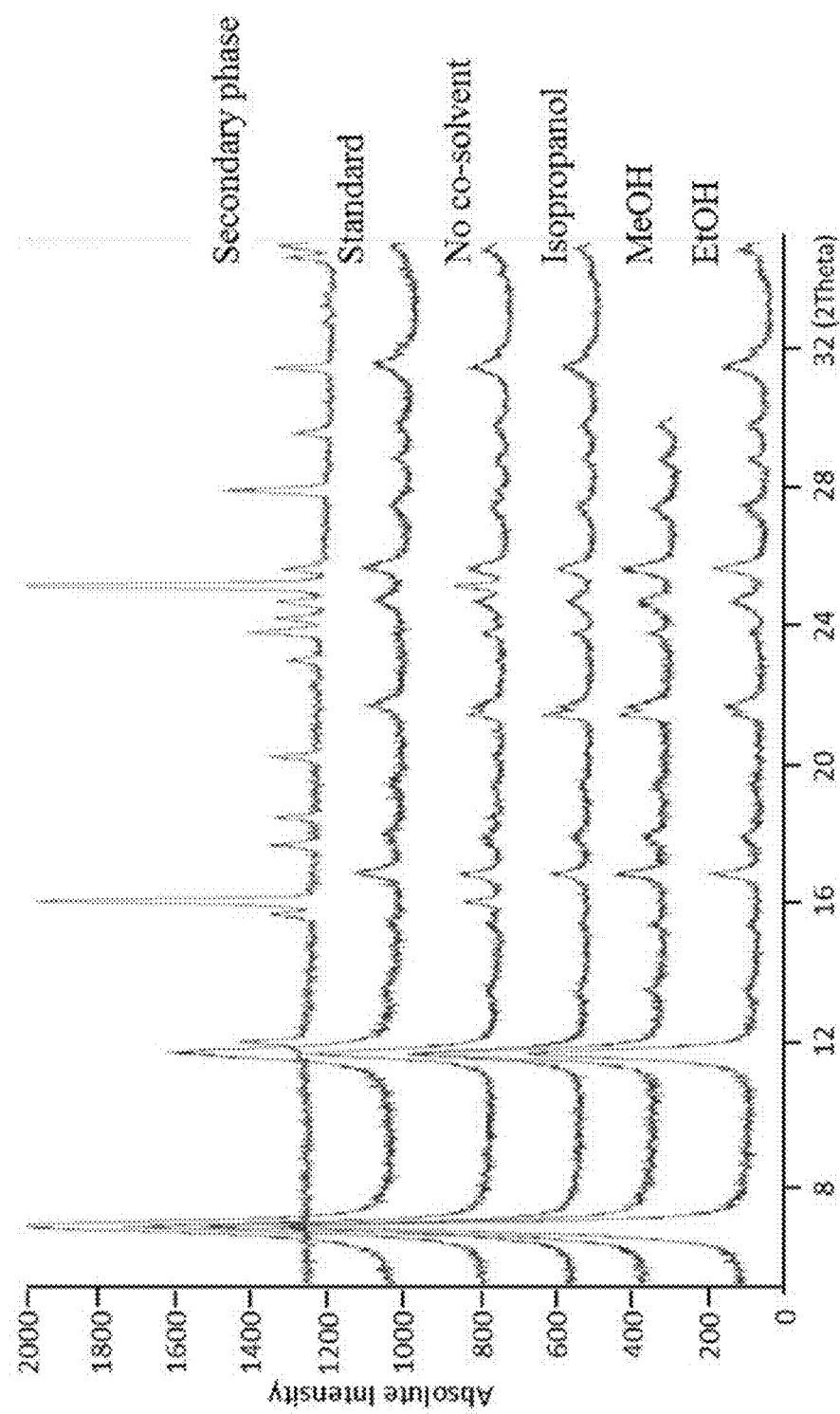
FIG. 1 shows XRD data for products prepared from Zn acetate with different co-solvents. The presence of an impurity phase is evident when no co-solvent is used.
Figure 2:
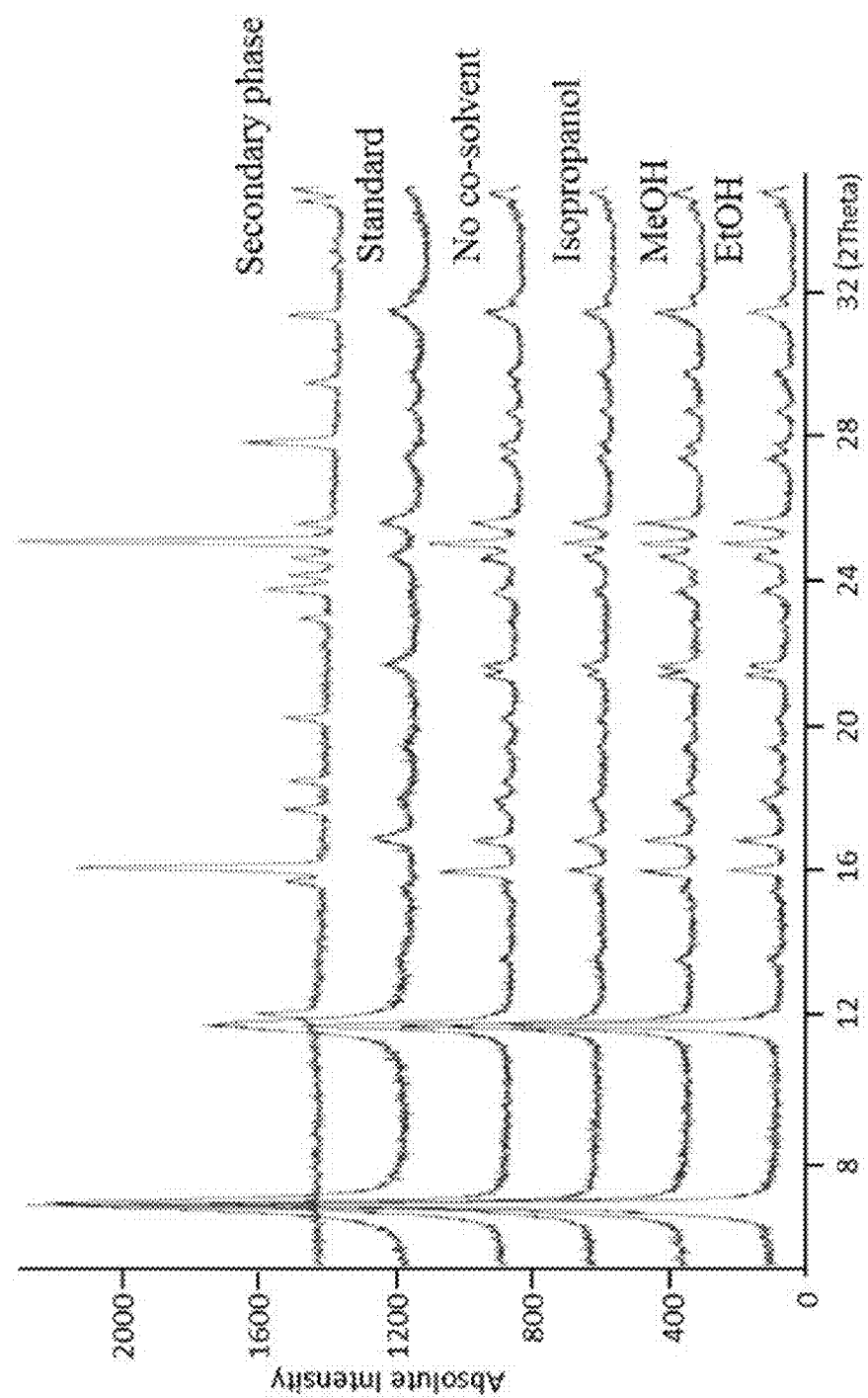
FIG. 2 shows XRD data for products prepared from Zn chloride with different co-solvents. The presence of an impurity phase is evident in all samples.
Figure 3:
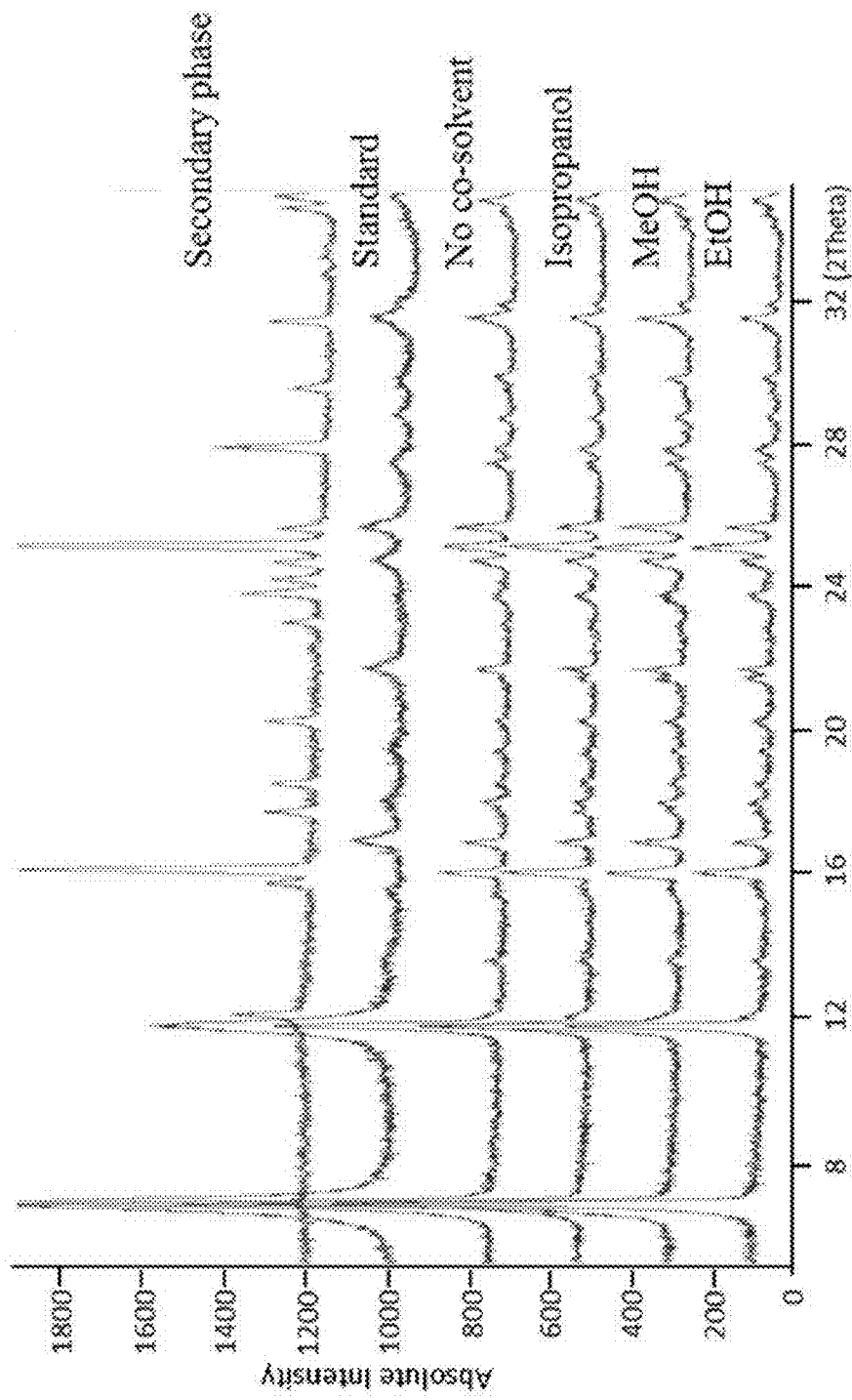
FIG. 3 shows XRD data for products prepared from Zn nitrate with different co-solvents. The presence of an impurity phase is evident in all samples.

Examples Relating to MOFs Containing DHTP Linkers
Preparation of Sodium 2,5-Dihydroxyterephthalate

Example 1

2,5-dihydroxyterephthalic acid (10 g, 50.5 mmol) was added to 1 molar aqueous sodium hydroxide solution (200 ml) with vigorous stirring. Once the acid dissolved, the sodium salt was precipitated by adding in excess of 200 ml of ethanol. The product was filtered and washed in ethanol before being refluxed in ethanol (200 ml, 80 C) for 2-3 hr. The solid was filtered hot, washed with hot ethanol and air dried.

Example 2

2,5-dihydroxyterephthalic acid (10 g, 50.5 mmol) was added to 1 molar aqueous sodium hydroxide solution (200 ml) with vigorous stirring. Once the acid dissolved, the sodium salt was recovered by evaporating off water under vacuum in a rotary evaporator. The product was refluxed in ethanol (200 ml, 80 C) for 2-3 hr, filtered hot, washed with hot ethanol and air dried.

Process 1

Example 3a: ZnNaDHTP

Sodium 2,5-dihydroxyterephthalate (0.48 g, 2 mmol) was dissolved in deionised (DI) water (15 ml) and the resulting solution was added dropwise over 3-5 min to a previously prepared aqueous solution of Zn acetate dihydrate (1.141 g, 5.2 mmol, in 7.5 ml DI water and 7.5 ml ethanol) under vigorous stirring. The mixture was stirred at 20 C for 4 hr before the product was recovered by filtration, washed in water (30 ml) and air dried.

TABLE 1

| Zn source | Co-solvent | Phase |
|---|---|---|
| Zn acetate | — | $Zn_xNa_z(dhtp)(H_2O)_g \cdot hH_2O$ + secondary phase |
|  | Ethanol | $Zn_xNa_z(dhtp)(H_2O)_g \cdot hH_2O$ |
|  | Methanol | $Zn_xNa_z(dhtp)(H_2O)_g \cdot hH_2O$ |
|  | Iso-propanol | $Zn_xNa_z(dhtp)(H_2O)_g \cdot hH_2O$ |
| Zn nitrate | — | $Zn_xNa_z(dhtp)(H_2O)_g \cdot hH_2O$ + secondary phase |
|  | Ethanol | $Zn_xNa_z(dhtp)(H_2O)_g \cdot hH_2O$ + secondary phase |
|  | Methanol | $Zn_xNa_z(dhtp)(H_2O)_g \cdot hH_2O$ + secondary phase |
|  | Iso-propanol | $Zn_xNa_z(dhtp)(H_2O)_g \cdot hH_2O$ + secondary phase |
| Zn chloride | — | $Zn_xNa_z(dhtp)(H_2O)_g \cdot hH_2O$ + secondary phase |
|  | Ethanol | $Zn_xNa_z(dhtp)(H_2O)_g \cdot hH_2O$ + secondary phase |
|  | Methanol | $Zn_xNa_z(dhtp)(H_2O)_g \cdot hH_2O$ + secondary phase |
|  | Iso-propanol | $Zn_xNa_z(dhtp)(H_2O)_g \cdot hH_2O$ + secondary phase |

Table 1 shows a summary of variations to Example 3a using different Zn sources and co-solvent showing that the phase purity depends on Zn source and co-solvent.

TABLE 2

Figure 4:
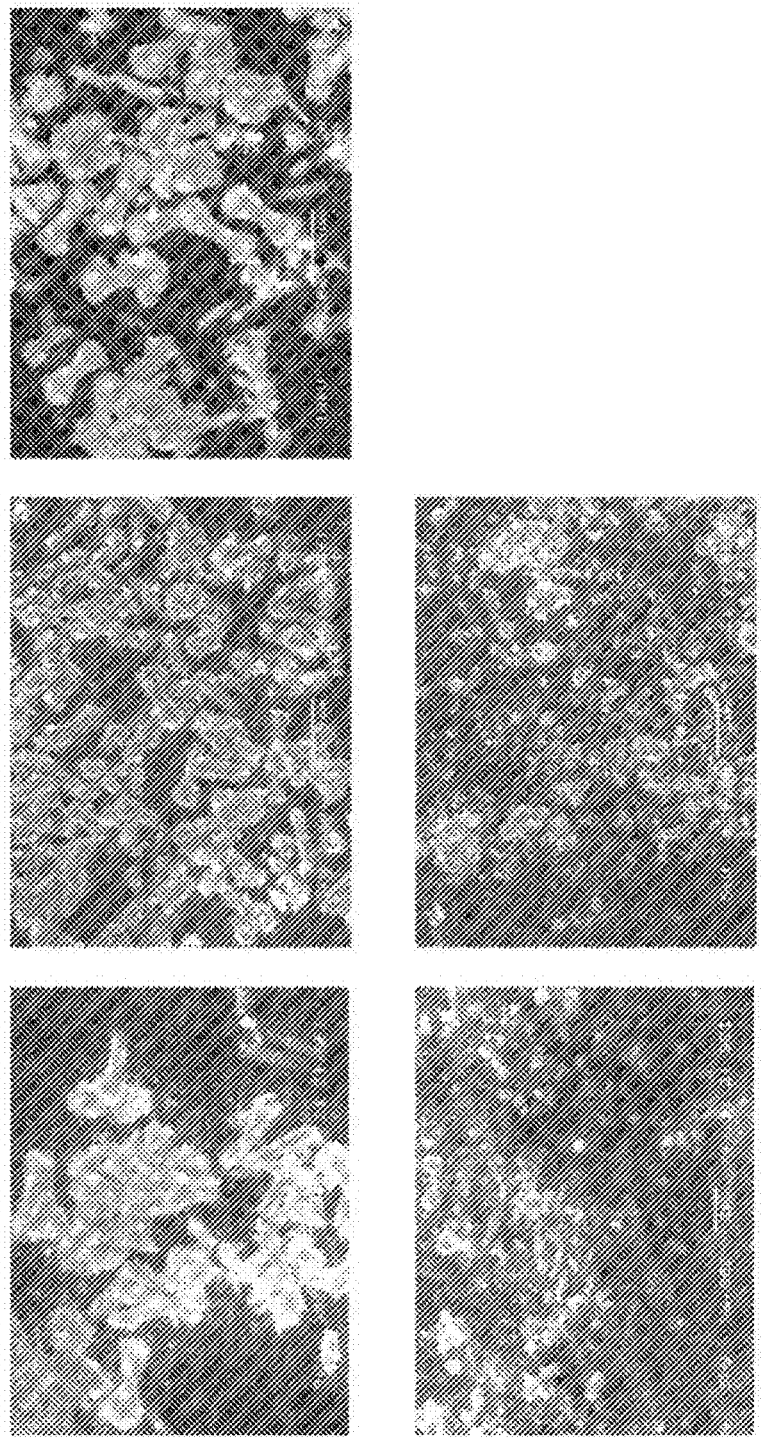
FIG. 4 shows SEM images of $Zn_xNa_z(dhtp)(H_2O)_g \cdot hH_2O$ prepared from reaction mixtures containing different Zn/linker (Zn/L) and water/ethanol (W/E) ratios. Top-left Zn/L 1, W/E 94; middle Zn/L 4.2 W/E 94; right Zn/L 2.6 W/E 9.7. Bottom-left Zn/L 1 W/E 3.5; right Zn/L 4.2 W/E 3.5.
Figure 5:
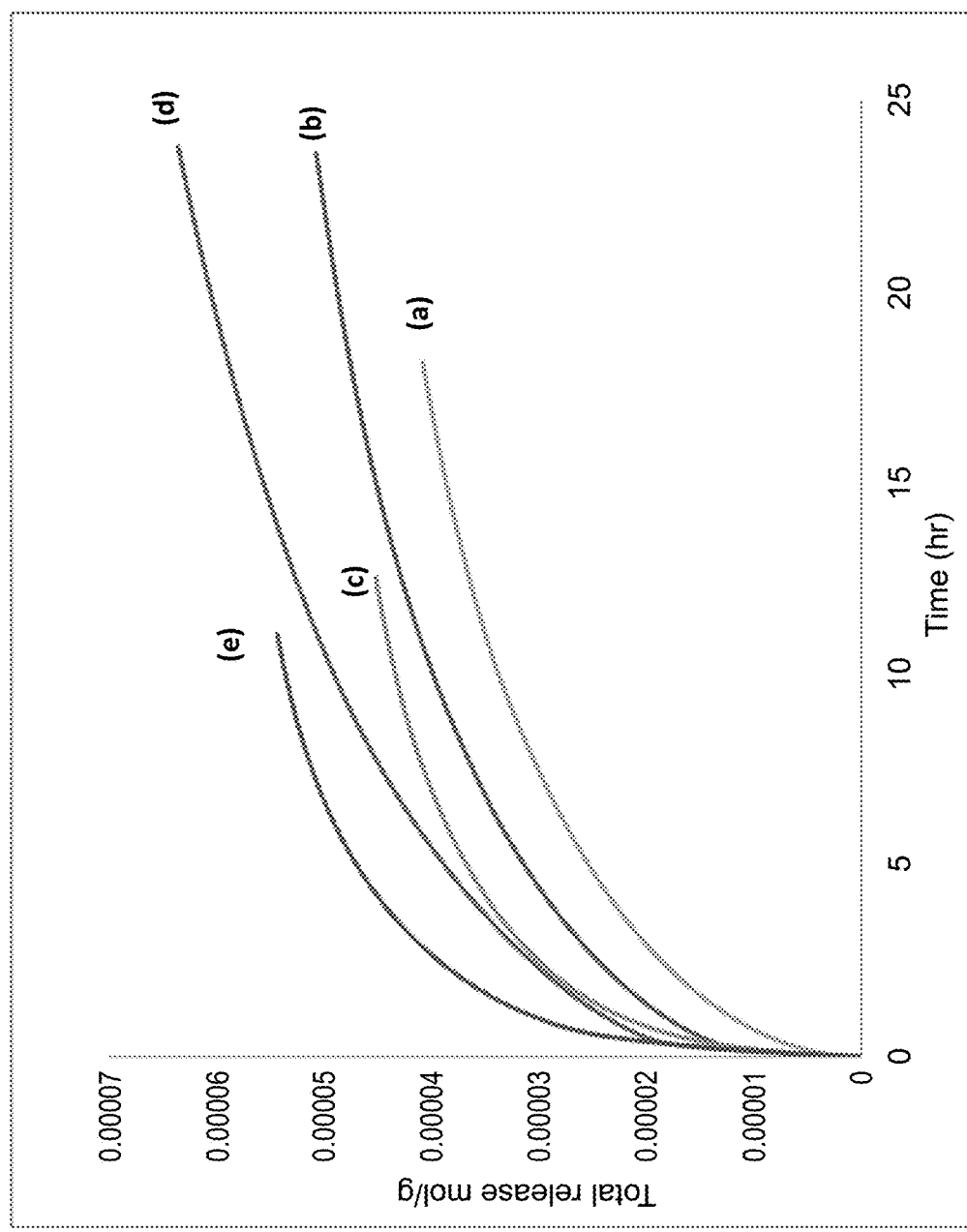
FIG. 5 shows NO release profiles for $Zn_xNa_z(dhtp)(H_2O)_g \cdot hH_2O$ synthesised as per example 3a and with different Zn/linker and water/ethanol ratios: (a) Zn/L 1 W/E 0.3; (b) Zn/L 1, W/E 94; (c) Zn/L 4.2 W/E 3.5; (d) Zn/L 4.2 W/E 94; (e) Zn/L 2.6 W/E 9.7.
Figure 6:
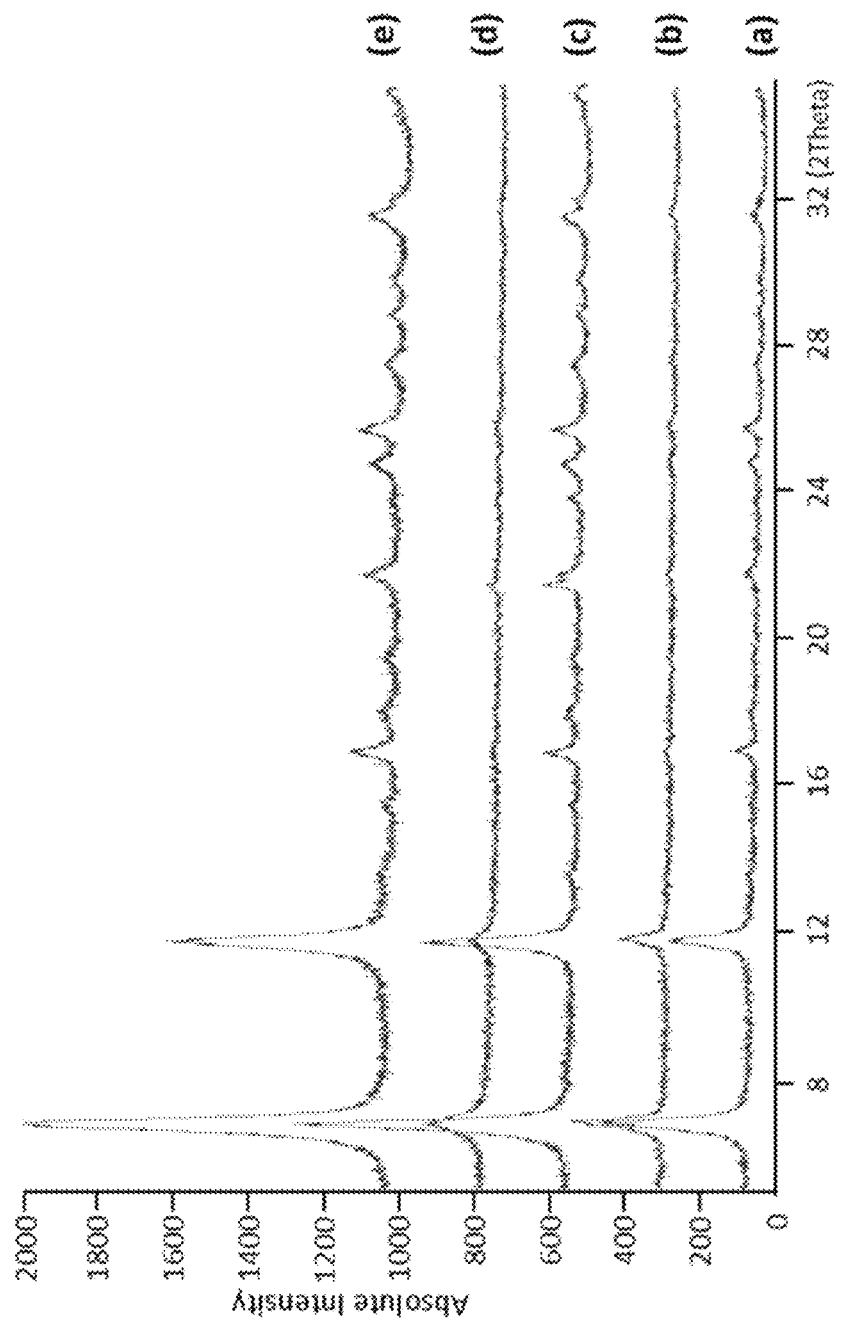
FIG. 6 shows XRD patterns of $Zn_xNa_z(dhtp)(H_2O)_g \cdot hH_2O$ synthesised as per example 3a and with different Zn/linker and water/ethanol ratios: (a) Zn/L 1, W/E 94; (b) Zn/L 1 W/E 3.5; (c) Zn/L 4.2 W/E 94; (d) Zn/L 4.2 W/E 3.5 (e) Zn/L 2.6 W/E 9.7.
Figure 7:
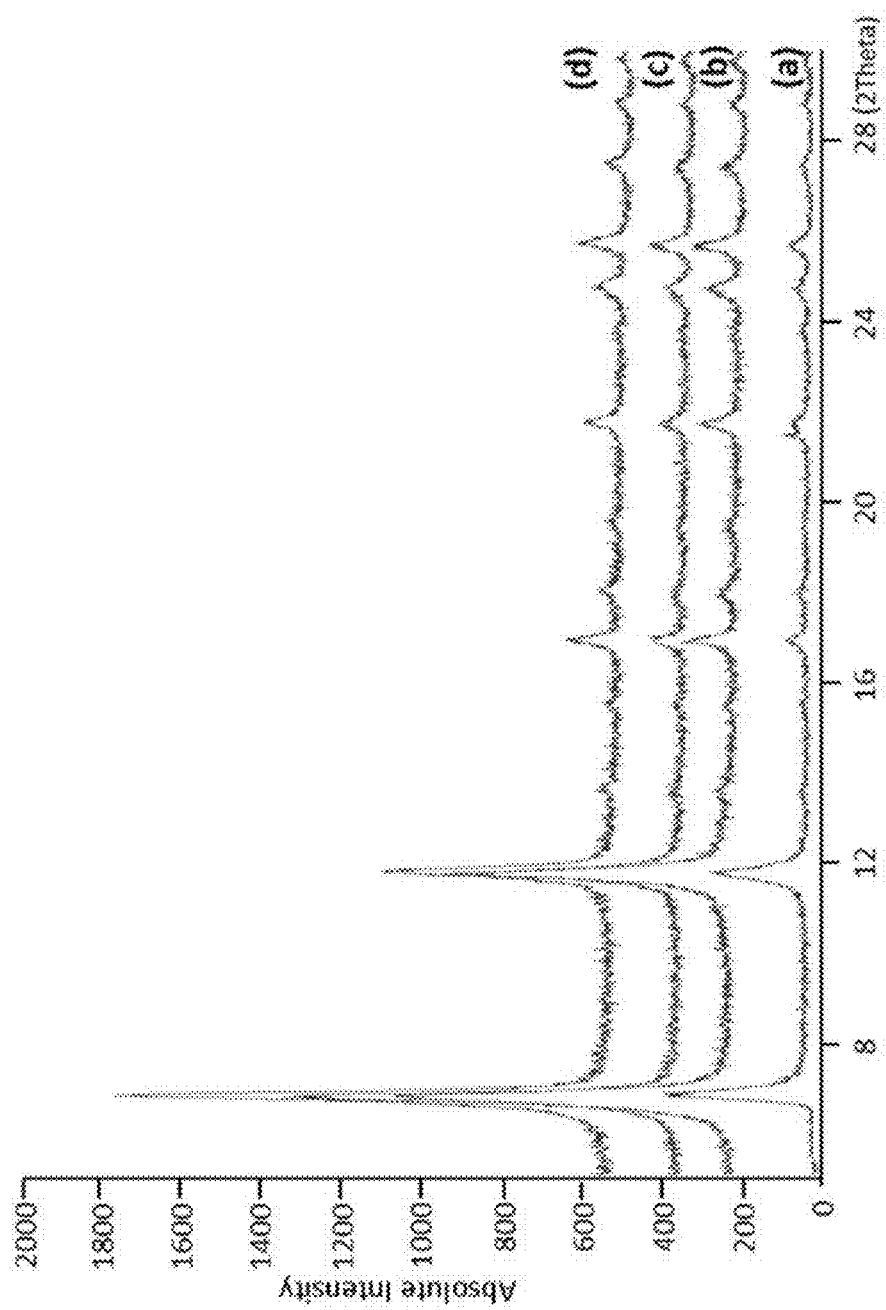
FIG. 7 shows XRD patterns for $Zn_xNa_z(dhtp)(H_2O)_g \cdot hH_2O$ prepared as per example 3a (a) over 1 hr, (b) over 5 hr, (c) over 48 hr and (d) at 50 deg C. over 1 hr.
Figure 8:
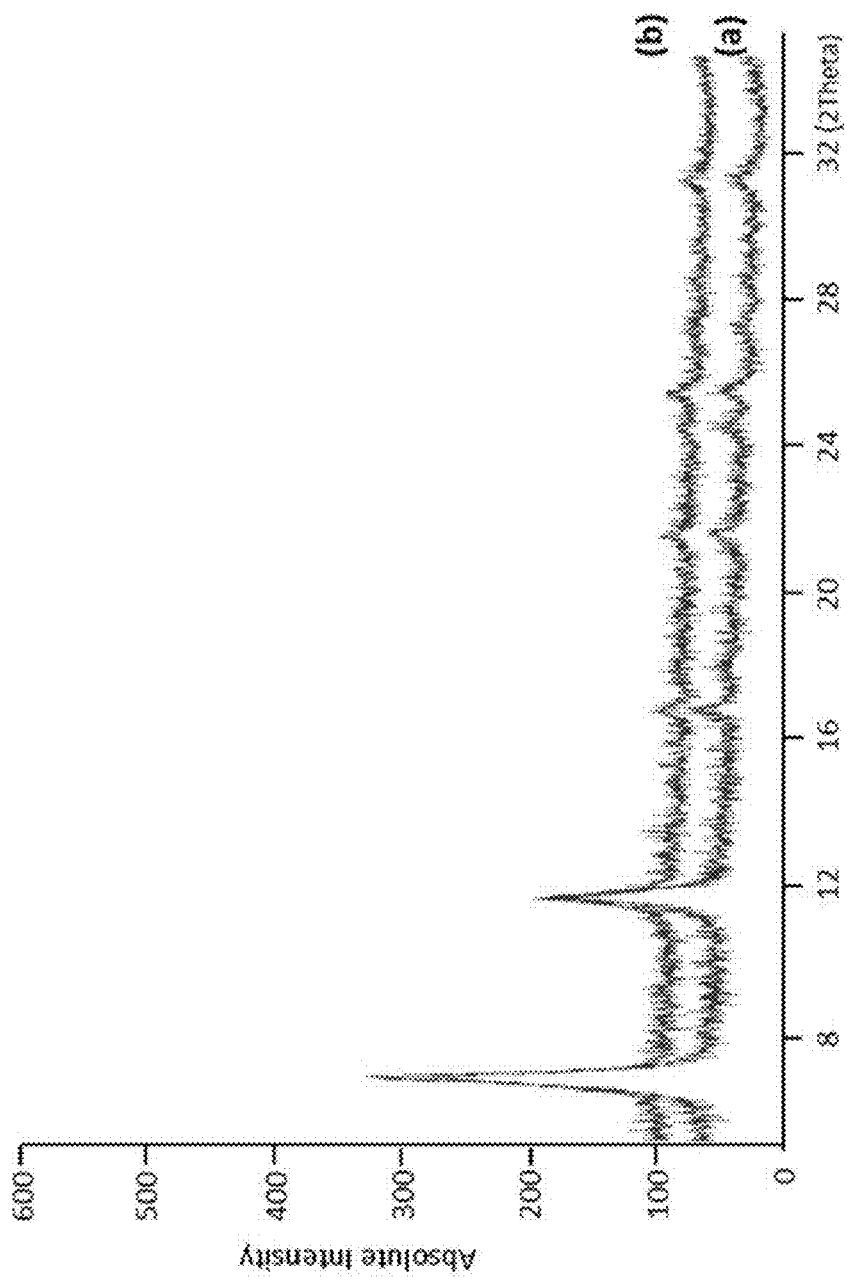
Figure 9:
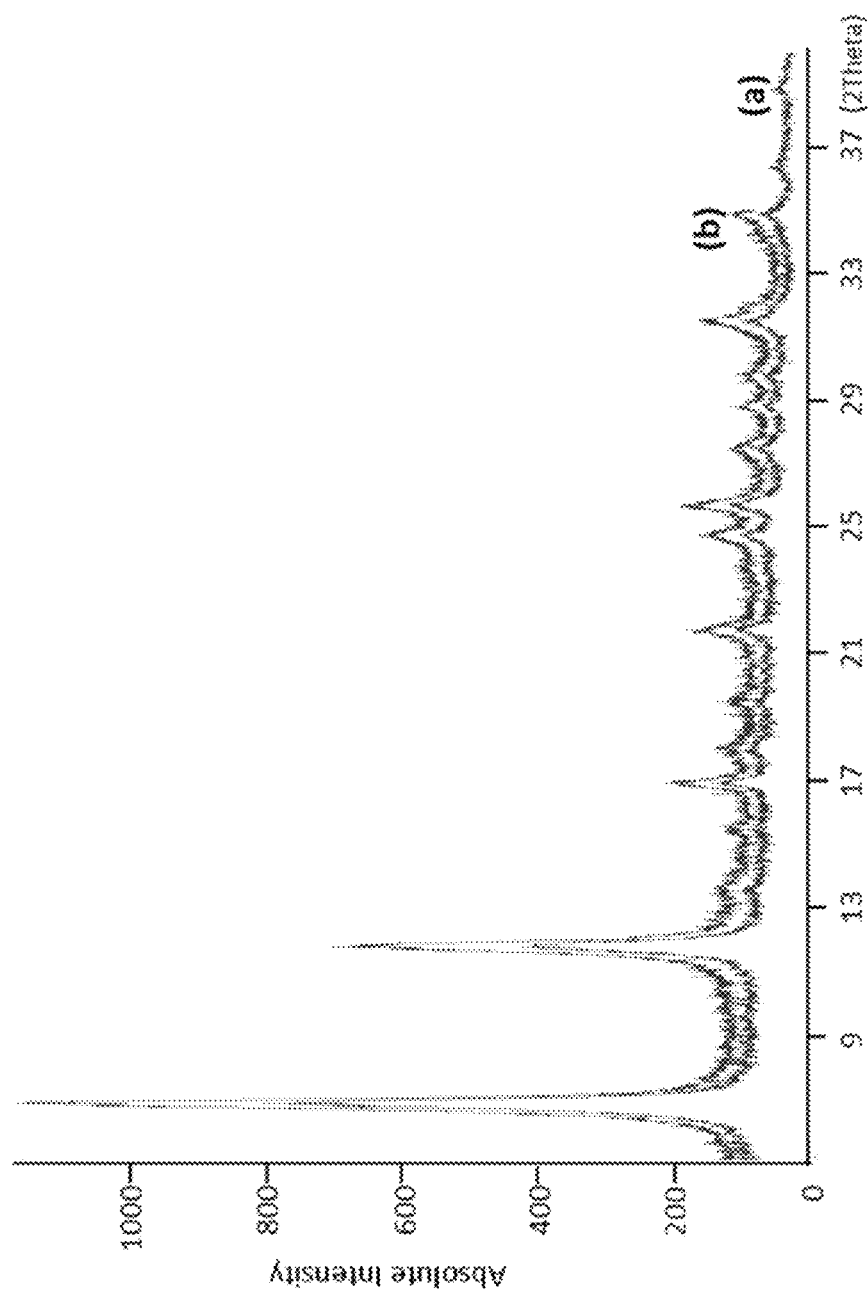
Figure 10:
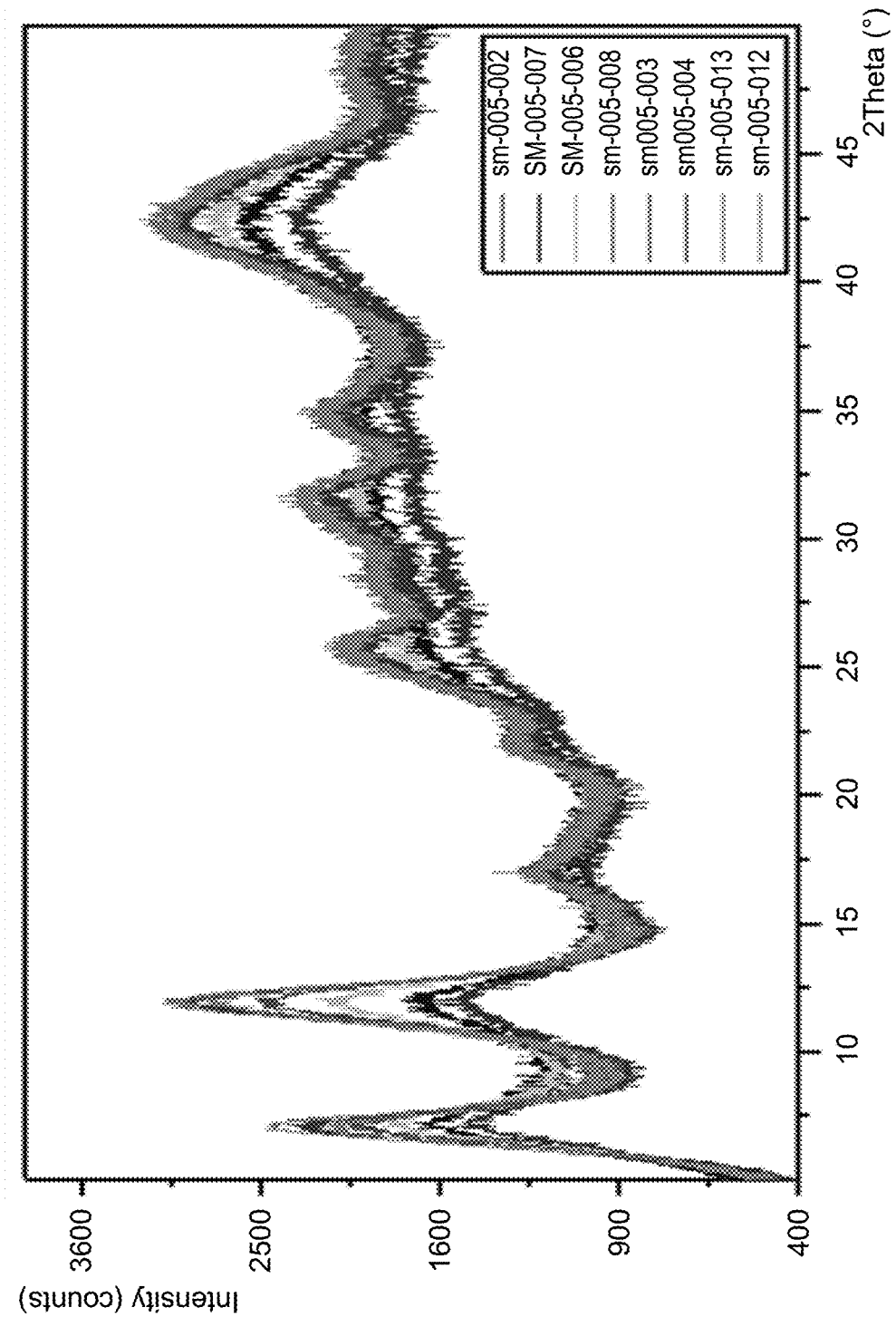
FIG. 10 shows XRD patterns of $Ni_yNa_z(dhtp)(H_2O)_g \cdot hH_2O$ synthesised as per example 4a with different reaction times as documented above. Data show that the phase does not change over time, although crystallinity may be affected.
Figure 11:
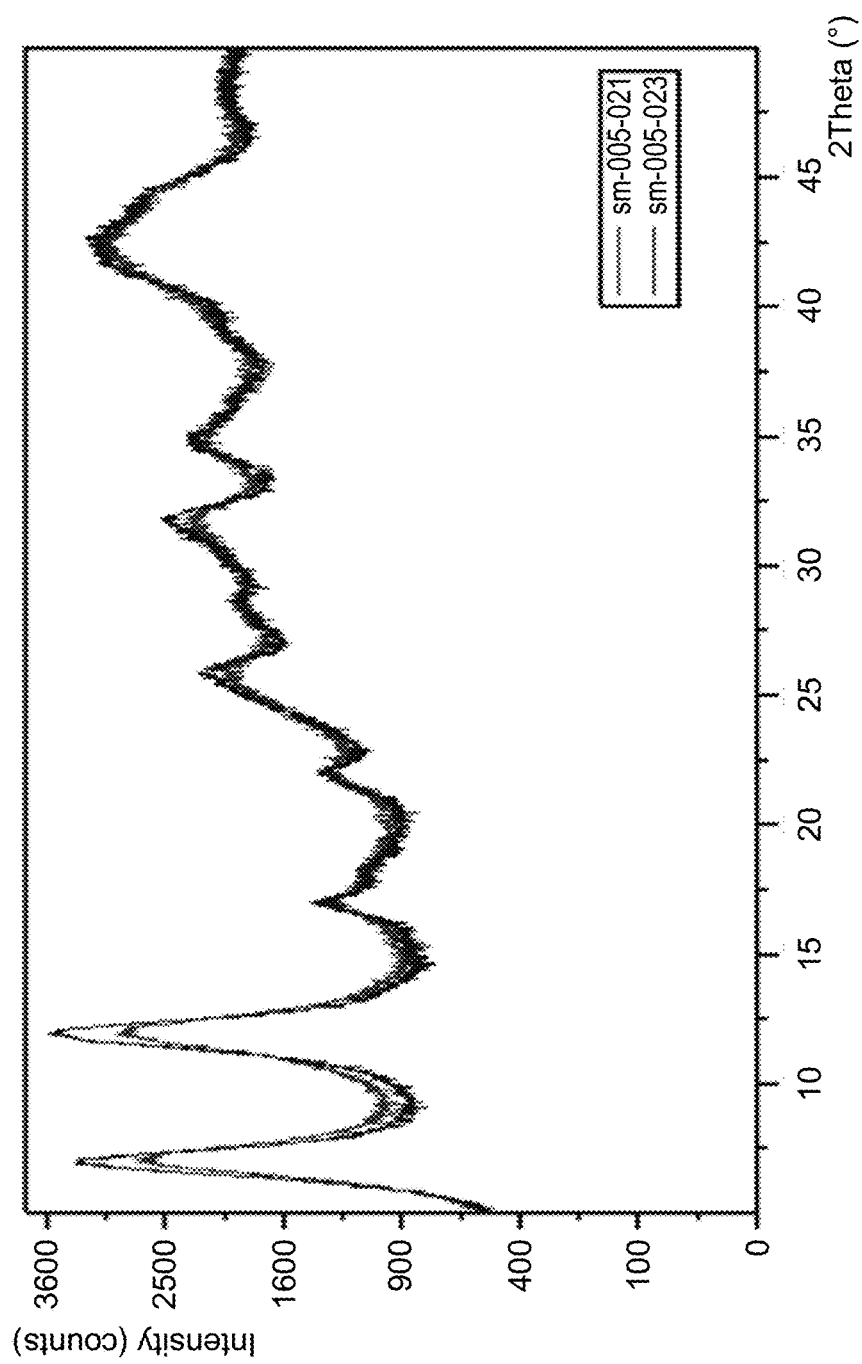
FIG. 11 shows XRD patterns for $Ni_yNa_z(dhtp)(H_2O)_g \cdot hH_2O$ synthesised as per Example 4b with 1 hr (red) and 4 hr (blue) reaction times. The data show that the same phase is obtained.
Figure 12:
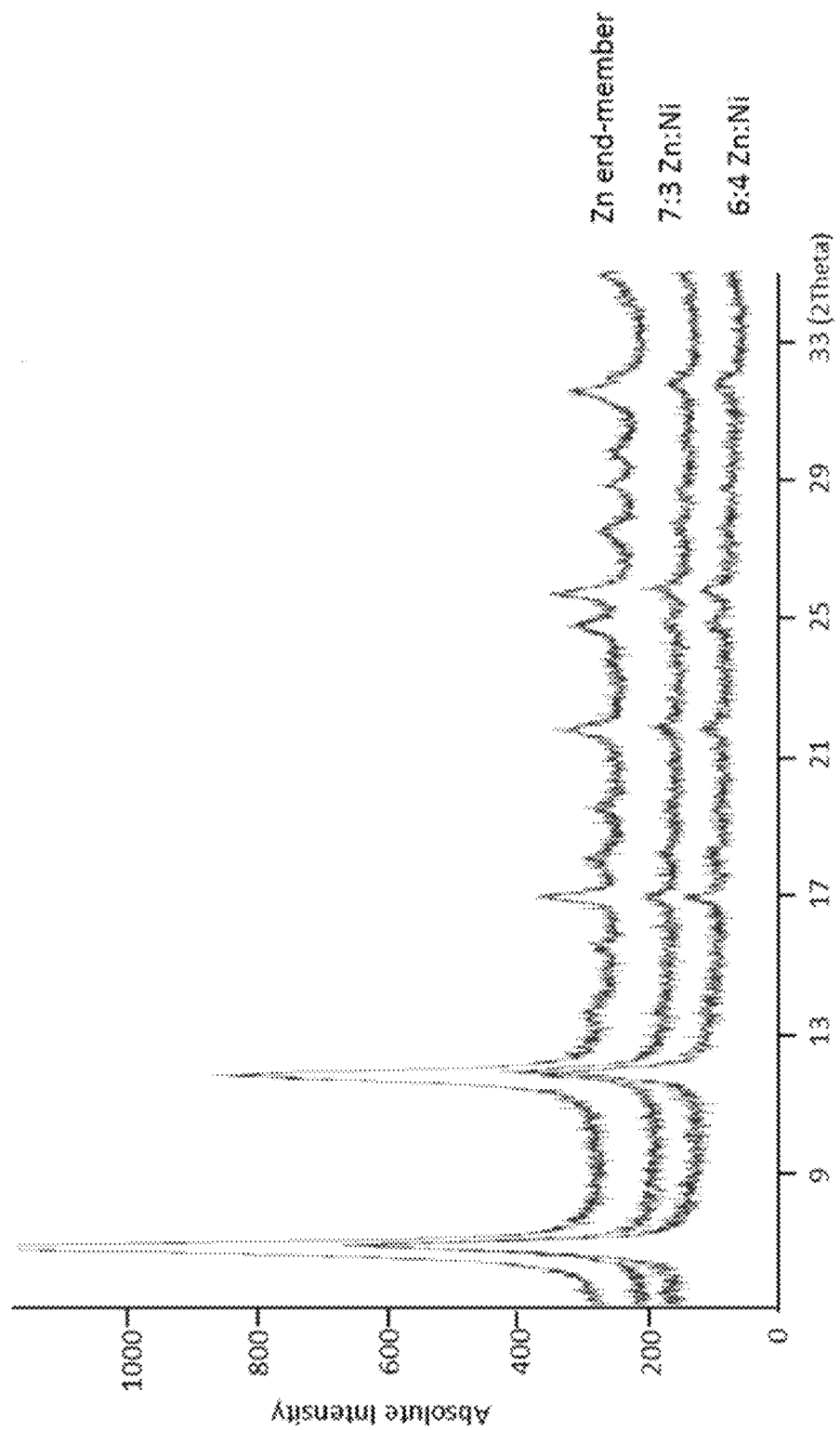
FIG. 12 shows XRD patterns of MOFs with compositions $Zn_2Na_{2.8}(DHTP)(H_2O)_2 \cdot qH_2O$ (top), $Zn_{1.47}Ni_{0.53}Na_{0.27}(DHTP)(H_2O)_2 \cdot qH_2O$ (middle) and $Zn_{1.49}Ni_{0.51}Na_{2.28}(DHTP)(H_2O)_2 \cdot qH_2O$ (bottom).
Figure 13:
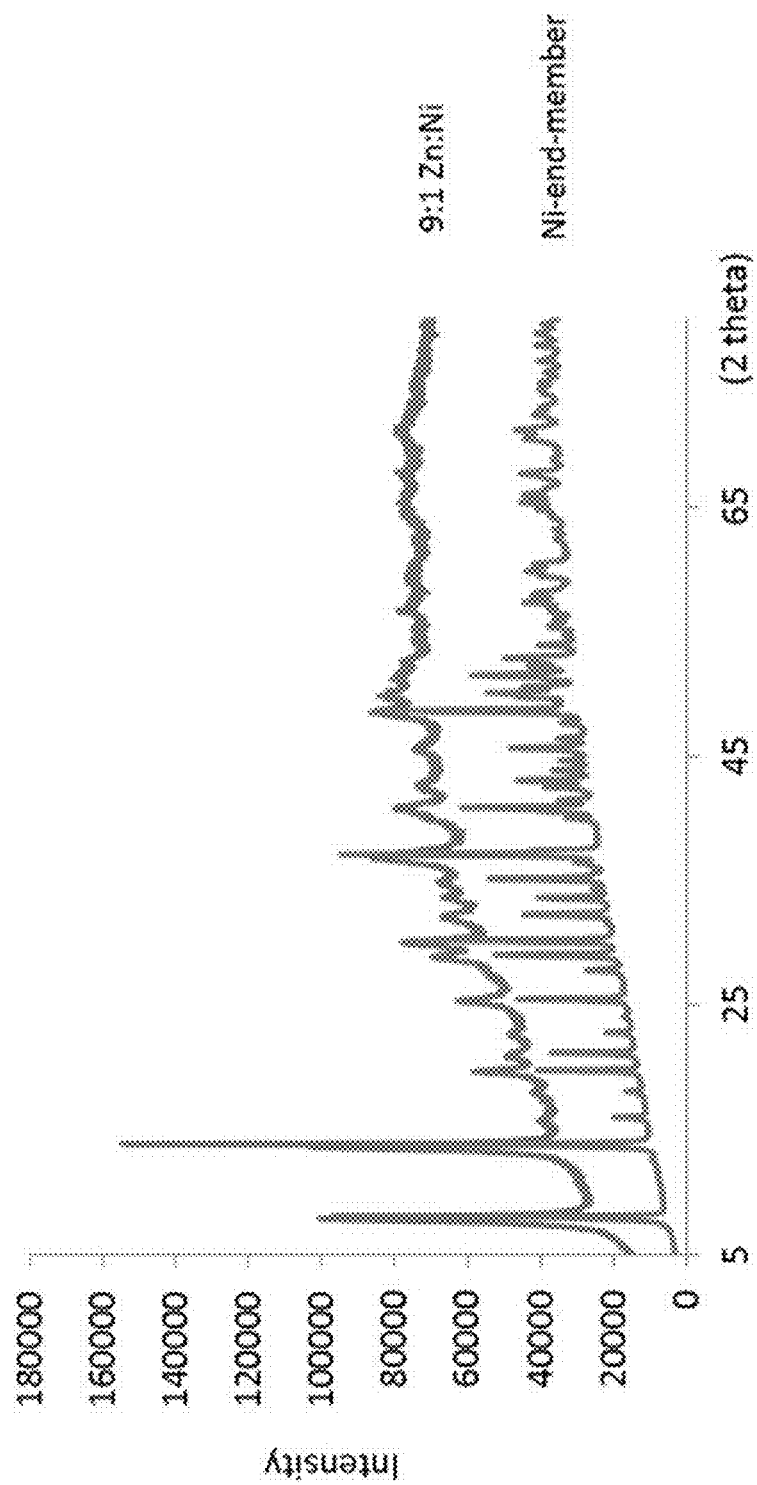
FIG. 13 shows XRD patterns of MOFs with compositions $Zn_{1.88}Ni_{0.12}Na_{3.22}(DHTP)(H_2O)_2 \cdot qH_2O$ (top) and $Ni_2Na_{28}(DHTP)(H_2O)_2 \cdot qH_2O$ (bottom).

| Zn/linker (mol ratio) | Water/ethanol (mol ratio) in final solution | Phase | Approx particle size (SEM)(μm) [see image in FIG. 4] | Yield (g) |
|---|---|---|---|---|
| 1 | 94 | $Zn_xNa_z(dhtp)(H_2O)_g \cdot hH_2O$ | 5 | 0.67 |
| 1 | 3.5 | $Zn_xNa_z(dhtp)(H_2O)_g \cdot hH_2O$ | <1 | 0.40 |
| 2.6 | 94 | $Zn_xNa_z(dhtp)(H_2O)_g \cdot hH_2O$ | No data | 0.53 |
| 2.6 | 9.7 | $Zn_xNa_z(dhtp)(H_2O)_g \cdot hH_2O$ | 5 | 0.48 |
| 2.6 | 3.5 | $Zn_xNa_z(dhtp)(H_2O)_g \cdot hH_2O$ | No data | 0.52 |
| 4.2 | 94 | $Zn_xNa_z(dhtp)(H_2O)_g \cdot hH_2O$ | 5 | 0.39 |
| 4.2 | 3.5 | $Zn_xNa_z(dhtp)(H_2O)_g \cdot hH_2O$ | <1 | 0.16 |

Table 2 shows summary of variations to Example 3a with different Zn/linker and water/ethanol ratios; the data show that solvent composition helps control particle size and yield.

TABLE 3

| Temperature (deg C.) | Time (hr) | Phase | Yield(g) |
|---|---|---|---|
| 20 | 1 | $Zn_xNa_z(dhtp)(H_2O)_g \cdot hH_2O$ | 0.48 |
|  | 5 | $Zn_xNa_z(dhtp)(H_2O)_g \cdot hH_2O$ | 0.53 |
|  | 24 | $Zn_xNa_z(dhtp)(H_2O)_g \cdot hH_2O$ | 0.56 |
|  | 48 | $Zn_xNa_z(dhtp)(H_2O)_g \cdot hH_2O$ | 0.54 |
| 50 | 1 | $Zn_xNa_z(dhtp)(H_2O)_g \cdot hH_2O$ | 0.37 |

Table 3 shows a summary of variations to Example 3a with different reaction temperatures.

Example 3b: ZnNaDHTP

Sodium 2,5-dihydroxyterephthalate (0.48 g, 2 mmol) was dissolved in DI water (15 ml) and the resulting solution was added swiftly to a previously prepared aqueous solution of Zn acetate dihydrate (1.141 g, 5.2 mmol, in 7.5 ml DI water and 7.5 ml ethanol) under vigorous stirring. The mixture was stirred at 20 C for 4 hr before the product was recovered by filtration, washed in water (30 ml) and air dried.

Example 4a: NiNaDHTP

Sodium 2,5-dihydroxyterephthalate (0.48 g, 2 mmol) was dissolved in DI water (15 ml) and the resulting solution was added dropwise over 3-5 min to a previously prepared aqueous solution of Ni acetate dihydrate (1.294 g, 5.2 mmol, in 7.5 ml DI water and 7.5 ml ethanol) under vigorous stirring. The mixture was stirred at 20 C for 7 hr before the product was recovered by filtration, washed in water (30 ml) and air dried.

TABLE 4

| Temperature (deg C.) | Time (hr) | Phase | Yield(g) |
|---|---|---|---|
| 20 | 1 | $Ni_yNa_z(dhtp)(H_2O)_g \cdot hH_2O$ | 0.34 |
| 20 | 2 | $Ni_yNa_z(dhtp)(H_2O)_g \cdot hH_2O$ | 0.42 |
| 20 | 4 | $Ni_yNa_z(dhtp)(H_2O)_g \cdot hH_2O$ | 0.46 |
| 20 | 7 | $Ni_yNa_z(dhtp)(H_2O)_g \cdot hH_2O$ | 0.52 |
| 20 | 18 | $Ni_yNa_z(dhtp)(H_2O)_g \cdot hH_2O$ | 0.58 |
| 20 | 24 | $Ni_yNa_z(dhtp)(H_2O)_g \cdot hH_2O$ | 0.61 |
| 20 | 28 | $Ni_yNa_z(dhtp)(H_2O)_g \cdot hH_2O$ | 0.58 |

Table 4 shows a summary of variations to Example 4a with different reaction times. The data show that the formation of the Ni end-member is generally slower than that for the Zn end-member—taking approx. 20 hr to reach maximum yield at 20 C.

Example 4b: NiNaDHTP

Sodium 2,5-dihydroxyterephthalate (0.48 g, 2 mmol) was dissolved in DI water (15 ml) and the resulting solution was added dropwise over 3-5 min to a previously prepared aqueous solution of Ni acetate dihydrate (1.294 g, 5.2 mmol, in 7.5 ml DI water and 7.5 ml ethanol) under vigorous stirring. The mixture was stirred at 50 C for 4 hr before the product was recovered by filtration, washed in water (30 ml) and air dried.

TABLE 5

| Temperature (deg C.) | Time (hr) | Phase | Yield(g) |
|---|---|---|---|
| 50 | 1 | $Ni_yNa_z(dhtp)(H_2O)_g \cdot hH_2O$ | 0.52 |
|  | 4 | $Ni_yNa_z(dhtp)(H_2O)_g \cdot hH_2O$ | 0.63 |
|  | 6 | $Ni_yNa_z(dhtp)(H_2O)_g \cdot hH_2O$ | 0.68 |

Table 5 shows a summary of variations to Example 4b with different reaction times showing that the process time can be reduced to a few hours by raising the temperature slightly to 50 C.

TABLE 6

| Ni/linker (mol ratio) | Water/co-solvent (mol ratio in final solution) | Phase | Yield(g) |
|---|---|---|---|
| 1.4 | 9.7 | $Ni_yNa_z(dhtp)(H_2O)_g \cdot hH_2O$ | 0.77 |
| 2 | 9.7 | $Ni_yNa_z(dhtp)(H_2O)_g \cdot hH_2O$ | 0.62 |
| 2.6 | 9.7 | $Ni_yNa_z(dhtp)(H_2O)_g \cdot hH_2O$ | 0.68 |
| 3.2 | 9.7 | $Ni_yNa_z(dhtp)(H_2O)_g \cdot hH_2O$ | 0.50 |

Table 6 shows a summary of variations to Example 4b with different Ni/Na linker ratios.

Example 4c: NiNaDHTP 2,5-dihydroxyterephthalic acid (2.02 g, 10.2 mmol) was added to aqueous sodium hydroxide (30 ml, 1.017M). The resulting solution was added dropwise over 15 min to a solution of Ni acetate dihydrate (5.10 g, 20.4 mmol) in DI water (30 ml). The mixture was stirred vigorously at 50 C for 6 hr before the product was recovered by filtration, washed in water (60 ml) and air dried.

Example 5: ZnNiNaDHTP

Sodium 2,5-dihydroxyterephthalate (0.48 g, 2 mmol) was dissolved in DI water (15 ml) and the resulting solution was added dropwise over 3-5 min to a previously prepared aqueous solution of Ni acetate dihydrate (0.129 g, 0.52 mmol) and Zn acetate dihydrate (1.027 g, 0.47 mmol) in 7.5 ml DI water and 7.5 ml ethanol, under vigorous stirring. The mixture was stirred at 20 C for 4 hr before the product was recovered by filtration, washed in water (30 ml) and air dried.

TABLE 7

| Zn/Ni mol % used in reaction | Approx Composition of product(EDX) | Average particle size (SEM) (μm) | NO released (mmol/g)/ time |
|---|---|---|---|
| 100/0 | $Zn_2Na_{2.8}(DHTP)(H_2O)_2 \cdot qH_2O$ | 5 | 0.05/12 hr |
| 90/10 | $Zn_{1.88}Ni_{0.12}Na_{3.22}(DHTP)(H_2O)_2 \cdot qH_2O$ | 5 | 0.3/18 hr |
| 80/20 | $Zn_{1.77}Ni_{0.23}Na_{3.93}(DHTP)(H_2O)_2 \cdot qH_2O$ | 3 |  |
| 70/30 | $Zn_{1.47}Ni_{0.53}Na_{0.27}(DHTP)(H_2O)_2 \cdot qH_2O$ | <1 | 0.3/45 hr |
| 60/40 | $Zn_{1.49}Ni_{0.51}Na_{2.28}(DHTP)(H_2O)_2 \cdot qH_2O$ | <1 | 0.7/17 hr |

Table 7 shows a summary of variations to Example 5 showing how particle size and NO release profile can be tuned by varying the Zn/Ni ratio

Process 2

Example 6: ZnNaDHTP

Zn acetate dihydrate (1.141 g, 5.2 mmol), DI water (22.5 ml), ethanol (7.5 ml) and sodium 2,5-dihydroxyterephthalate (0.48 g, 2 mmol), were mixed together. The mixture was stirred vigorously at 20 C for 4 hr before the product was recovered by filtration, washed in water (30 ml) and air dried.

Example 7: ZnNaDHTP

Zn acetate dihydrate (3.5 g, 16 mmol), DI water (22.5 ml), ethanol (7.5 ml) and sodium 2,5-dihydroxyterephthalate (1.49 g, 6.2 mmol), were mixed together. The mixture was stirred vigorously at 20 C for 4 hr before the product was recovered by filtration, washed in water (30 ml) and air dried.

Example 8: ZnNaDHTP

Zn acetate dihydrate (7 g, 0.032 mol), DI water (22.5 ml), ethanol (7.5 ml) and sodium 2,5-dihydroxyterephthalate (2.97 g, 0.012 mol), were mixed together. The mixture was stirred vigorously at 20 C for 4 hr before the product was recovered by filtration, washed in water (30 ml) and air dried.

Example 9: NiNaDHTP

Ni acetate dihydrate (1.027 g, 0.47 mmol), DI water (22.5 ml), ethanol (7.5 ml) and sodium 2,5-dihydroxyterephthalate (0.48 g, 2 mmol), were mixed together. The mixture was stirred vigorously at 20 C for 4 hr before the product was recovered by filtration, washed in water (30 ml) and air dried.

Process 3

Example 10: ZnNaDHTP a) 2,5-dihydroxyterephthalic acid (0.51 g, 2.6 mmol) was added to aqueous sodium hydroxide (15 ml, 0.67M). A solution of Zn acetate dihydrate (1.141 g, 5.2 mmol) in DI water (7.5 ml) and ethanol (7.5 ml) was added dropwise to the resulting solution over 3-5 min with stirring. The mixture was stirred vigorously at 20 C for 4 hr before the product was recovered by filtration, washed in water (30 ml) and air dried.

b) 2,5-dihydroxyterephthalic acid (0.51 g, 2.6 mmol) was added to aqueous sodium hydroxide (15 ml, 0.52M). A solution of Zn acetate dihydrate (1.141 g, 5.2 mmol) in DI water (7.5 ml) and ethanol (7.5 ml) was added dropwise to the resulting solution over 3-5 min with stirring. The mixture was stirred vigorously at 20 C for 4 hr before the product was recovered by filtration, washed in water (30 ml) and air dried.

Example 11a: ZnNaDHTP

Zn acetate dihydrate solution (1.141 g, 5.2 mmol, in 7.5 ml DI water and 7.5 ml ethanol) was added dropwise over 3-5 min to a previously prepared solution of sodium 2,5-dihydroxyterephthalate (0.48 g, 2 mmol) in DI water (15 ml) under vigorous stirring. The mixture was stirred at 20 C for 4 hr before the product was recovered by filtration, washed in water (30 ml) and air dried.

Example 11b: ZnNaDHTP 2,5-dihydroxyterephthalic acid (1.03 g, 5.2 mmol) was added to aqueous sodium hydroxide (30 ml, 0.35M) and heated to 60 C. To the resulting solution was added Zn acetate dihydrate (2.96 g, 13.5 mmol) in DI water (15 ml) and ethanol (15 ml), dropwise over 25 min, with stirring. The mixture was stirred vigorously at 60 C for 4 hr before the product was recovered by filtration, washed in water (30 ml) and air dried.

Example 12: ZnNaDHTP 2,5-dihydroxyterephthalic acid (0.39 g, 2 mmol), sodium hydroxide (0.16 g, 4 mmol) and then Zn acetate dihydrate (1.141 g, 5.2 mmol) was dissolved in DI water (22.5 ml) and ethanol (7.5 ml) with stirring. The mixture was stirred vigorously at 20 C for 4 hr before the product recovered by filtration, washed in water (30 ml) and air dried.

Example 13: ZnNaDTHP; Higher Concentration Synthesis 2,5-dihydroxyterephthalic acid (2.3 g, 11.8 mmol) was dissolved in aqueous sodium hydroxide (24 ml, 2M) at 60 C. A solution of Zn acetate dihydrate (8 g, 36.5 mmol) in DI water (13 ml) and ethanol (4.3 ml), also at 60 C, was added dropwise to the resulting solution over 3-5 min with stirring. The mixture was stirred vigorously at 60 C for 3 hr before the product was recovered by filtration, washed in water (30 ml) and air dried.

Example 14: NiNaDHTP 2,5-dihydroxyterephthalic acid (2.02 g, 10.2 mmol) was added to aqueous sodium hydroxide (30 ml, 1.017M). To the resulting solution Ni acetate dihydrate (5.10 g, 20.4 mmol) in DI water (30 ml) was added dropwise over 15 min. The mixture was stirred vigorously at 50 C for 6 hr before the product was recovered by filtration, washed in water (60 ml) and air dried.

Example 15: NiNaDHTP a) 2,5-dihydroxyterephthalic acid (0.51 g, 2.6 mmol) was added to aqueous sodium hydroxide (15 ml, 0.67M). A solution of Ni acetate dihydrate (1.296 g, 5.2 mmol) in DI water (15 ml) was added dropwise to the resulting solution over 3-5 min with stirring. The mixture was stirred vigorously at 50 C for 6 hr before the product was recovered by filtration, washed in water (30 ml) and air dried.

b) 2,5-dihydroxyterephthalic acid (0.51 g, 2.6 mmol) was added to aqueous sodium hydroxide (15 ml, 0.52M). A solution of Ni acetate dihydrate (1.296 g, 5.2 mmol) in DI water (15 ml) was added dropwise to the resulting solution over 3-5 min with stirring. The mixture was stirred vigorously at 50 C for 6 hr before the product was recovered by filtration, washed in water (30 ml) and air dried.

Examples Relating to MOFs Containing BTC Linkers

Materials were prepared according to three general synthetic procedures (A)-(C) described below.

Synthesis Procedure (A)

A basic solution (such as aqueous sodium hydroxide, potassium hydroxide, or organic bases such as ammonia, trimethylamine, triethylamine or similar) is added to a suspension of trimesic acid in water (preferably distilled or de-ionised) until the desired pH is achieved at which the suspended trimesic acid dissolves (typically pH 7 and above, depending on the basic solution used). A solution of a metal salt is then added at the required rate under brisk stirring. The invention is not limited to a particular metal salt or salts, or solvent. For the preparation of Ag-BTC MOFs, silver nitrate in distilled water is preferred, in order to minimise use of organic solvents. On mixing of the two solutions at a temperature typically in the range 2-100° C. or 18-30° C., a precipitate is formed which is recovered after a period of time (e.g. 1 min to 2 days, or more preferably in the range 20-120 min). Precipitate is recovered by any suitable method, (e.g. filtration). In an optional purification step, the product is washed with one or more solvents (e.g. water then ethanol), and air dried. Examples 16-25 of preparing a Ag-BTC MOF by method (A) are set out below.

Example 16

1M sodium hydroxide solution was added dropwise to a suspension of trimesic acid (1.007 g, 4.8 mmol) in distilled 75 ml water to a phenolphthalein end-point (pH7). To this was added a solution of silver nitrate (3.5 equivalents) in 12.5 ml distilled water, dropwise with stirring at 20° C. After 45 min the product was recovered by filtration, washed with distilled water, then ethanol and air dried.

Example 17

1M sodium hydroxide solution was added dropwise to a suspension of trimesic acid (1.007 g, 4.8 mmol) in distilled 75 ml water to achieve pH 10. To this was added a solution of silver nitrate (3.5 equivalents) in 12.5 ml distilled water, dropwise with stirring at 20° C. After 45 min the product was recovered by filtration, washed with distilled water, then ethanol and air dried.

Example 18

1M sodium hydroxide solution was added dropwise to a suspension of trimesic acid (1.007 g, 4.8 mmol) in distilled 75 ml water to achieve pH 6. To this was added a solution of silver nitrate (3.5 equivalents) in 12.5 ml distilled water, dropwise with stirring at 20° C. After 45 min the product was recovered by filtration, washed with distilled water, then ethanol and air dried.

Example 19

1M sodium hydroxide solution was added dropwise to a suspension of trimesic acid (1.007 g, 4.8 mmol) in distilled 75 ml water to a phenolphthalein end-point. To this was added a solution of silver nitrate (3.5 equivalents) in 12.5 ml distilled water, quickly with stirring at 20° C. After 45 min the product was recovered by filtration, washed with distilled water, then ethanol and air dried.

Example 20

1M sodium hydroxide solution was added dropwise to a suspension of trimesic acid (1.007 g, 4.8 mmol) in distilled 75 ml water to a phenolphthalein end-point. This solution was added to a solution of silver nitrate (3.5 equivalents) in 12.5 ml distilled water, dropwise with stirring at 20° C. After 45 min the product was recovered by filtration, washed with distilled water, then ethanol and air dried.

Example 21

1M sodium hydroxide solution was added dropwise to a suspension of trimesic acid (1.007 g, 4.8 mmol) in distilled 75 ml water to a phenolphthalein end-point. This solution was added to a solution of silver nitrate (3.5 equivalents) in 12.5 ml distilled water, quickly with stirring at 20° C. After 45 min the product was recovered by filtration, washed with distilled water, then ethanol and air dried.

Example 22a 1M sodium hydroxide solution was added dropwise to a suspension of trimesic acid (1.007 g, 4.8 mmol) in distilled 75 ml water to a phenolphthalein end-point. To this was added a solution of silver nitrate (3.5 equivalents) in 12.5 ml distilled water, dropwise with stirring at 60° C. After 45 min the product was recovered by filtration, washed with distilled water, then ethanol and air dried.

Example 22b

Figure 22A:
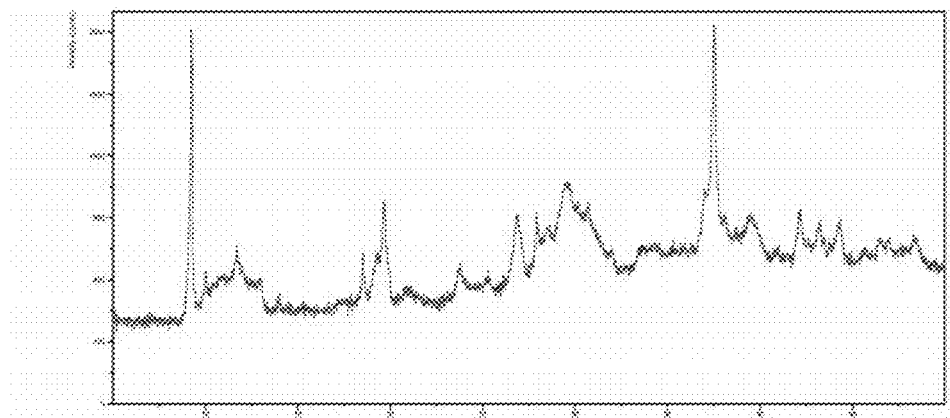
FIGS. 22(a)-(c) show powder XRD pattern of the Ag-BTC MOFs prepared according to examples 22(a)-(c).
Figure 22B:
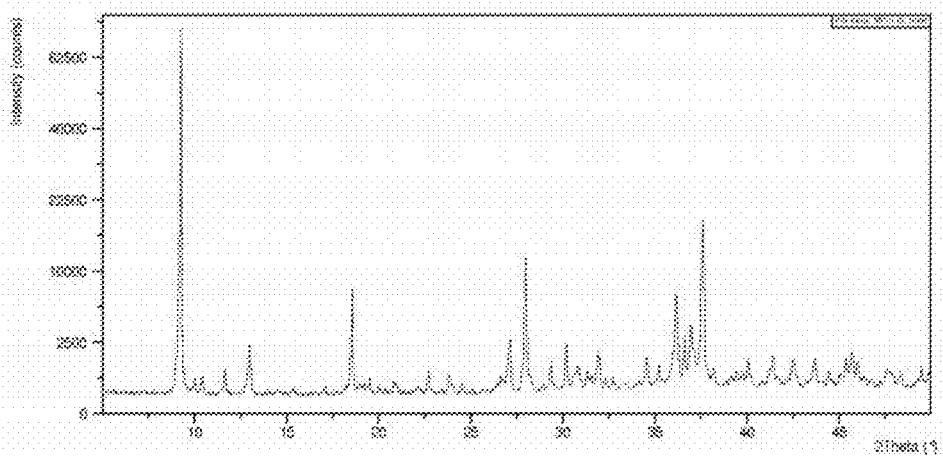
Figure 22C:
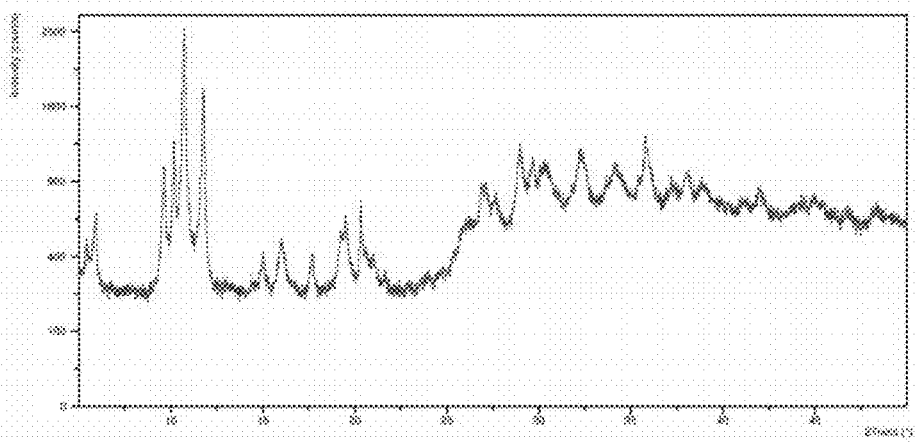
Figure 23:
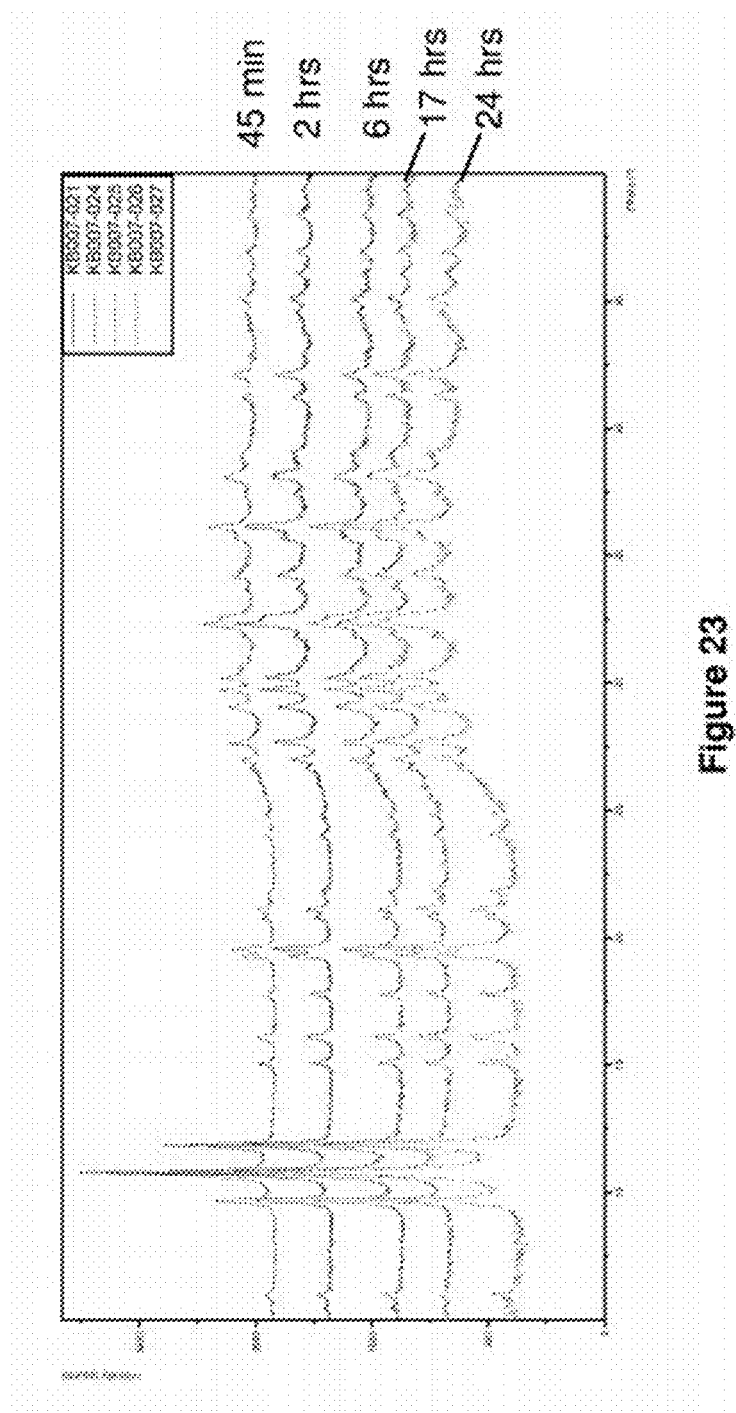
FIG. 23 shows powder XRD patterns of the Ag-BTC MOF prepared according to example 23, with crystallisation periods of (top to bottom) 45 min, 2, 6, 17, 24 hr.
Figure 24:
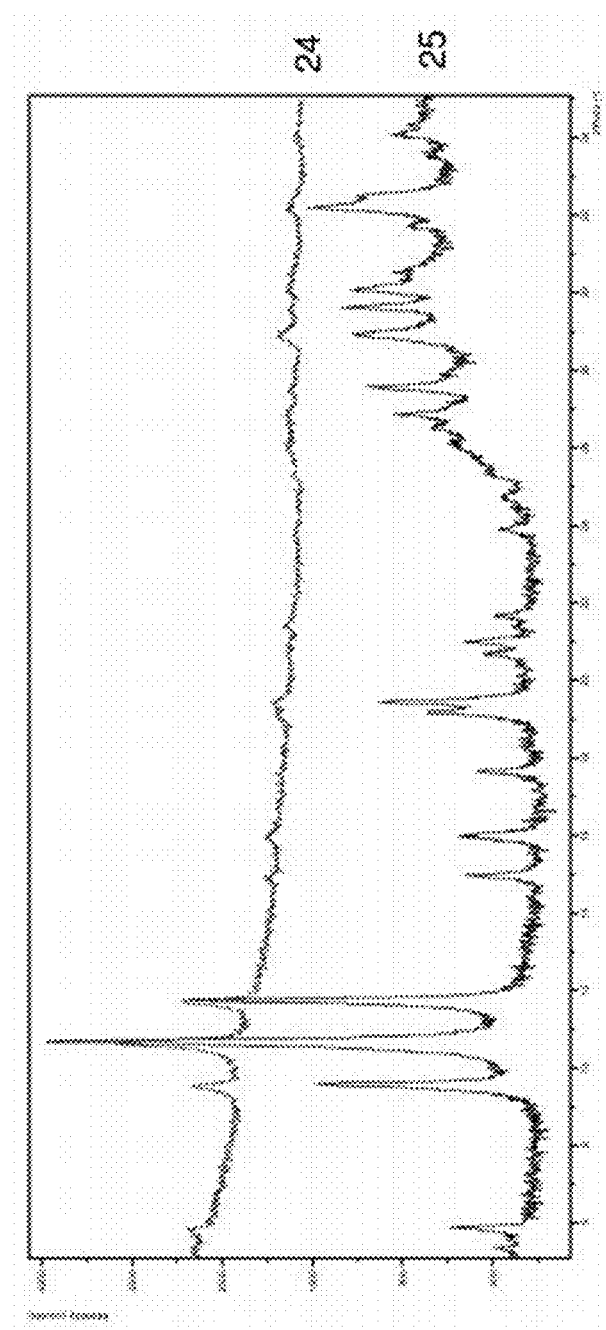
FIG. 24 shows powder XRD patterns of the Ag-BTC MOF prepared according to examples 24 (top) and 25 (bottom).

Trimesic acid (5 g, 23.8 mmol) was dissolved in aqueous sodium hydroxide (71.4 ml, 1M) under reflux. Once dissolved, the solution was cooled to 60° C. before a solution of silver nitrate (12 g, 70.6 mmol) in water (100 ml) was added. After stirring at 60° C. for 4 hr, the product was recovered by filtration, washed with distilled water, then ethanol and air dried. Approximate product composition of material synthesised in this manner was found to be in the range $Ag_{2-4}(BTC)_{0.5-2} \cdot 1\text{-}3H_2O$ (as determined from single crystal XRD and TGA studies). Powder XRD data (FIG. 22(b)) and single crystal XRD data indicate that the material is a new phase and differs from the materials synthesised at a lower temperature (examples 22a and 22c).

Example 22c

Trimesic acid (5 g, 23.8 mmol) was dissolved in aqueous sodium hydroxide (71.4 ml, 1M) under reflux. Once dissolved, the solution was cooled to room temperature before a solution of silver nitrate (12 g, 70.6 mmol) in water (100 ml) was added. After stirring at room temperature for 4 hr, the product was recovered by filtration, washed with distilled water, then ethanol and air dried.

Example 23

1M sodium hydroxide solution was added dropwise to a suspension of trimesic acid (1.007 g, 4.8 mmol) in distilled 75 ml water to a phenolphthalein end-point. To this was added a solution of silver nitrate (3.5 equivalents) in 12.5 ml distilled water, dropwise with stirring at 20° C. After 20 min, 1 hr, 5 hr. 16 hr and 24 hr the product was recovered by filtration, washed with distilled water, then ethanol and air dried.

Example 24. (1:14)

1M sodium hydroxide solution was added dropwise to a suspension of trimesic acid (0.503 g, 2.4 mmol) in distilled 75 ml water to a phenolphthalein end-point. To this was added a solution of silver nitrate (14 equivalents) in 50 ml distilled water, dropwise with stirring at 20° C. After 45 min the product was recovered by filtration, washed with distilled water, then ethanol and air dried.

Example 25. (1:1)

1M sodium hydroxide solution was added dropwise to a suspension of trimesic acid (1.131 g, 5.4 mmol) in distilled 75 ml water to a phenolphthalein end-point. To this was added a solution of silver nitrate (1 equivalent) in 12.5 ml distilled water, dropwise with stirring at 20° C. After 45 min the product was recovered by filtration, washed with distilled water, then ethanol and air dried.

Example 26

Trimesic acid (5 g, 23.8 mmol) was dissolved in NaOH (1M, 74.1 mL) and water (218.8 mL) at 30° C. Once dissolved, the pH was adjusted to 7 using nitric acid before silver nitrate (12 g, 70.6 mmol) in water (100 mL) was charged rapidly to the flask. After stirring at 30° C. for 2.5 hr, the product was recovered by filtration, washed with distilled water, then ethanol and air dried.

Example 27. [Slower Addition Rate]

Trimesic acid (5 g, 23.8 mmol) was dissolved in NaOH (1M, 74.1 mL) and water (218.8 mL) at 30° C. Once dissolved, the pH was adjusted to 7 using nitric acid before silver nitrate (12 g, 70.6 mmol) in water (100 mL) was charged over 10 min to the flask. After stirring at 30° C. for 2.5 hr, the product was recovered by filtration, washed with distilled water, then ethanol and air dried.

XRPD data indicate that examples 26 and 27 produced the same phase as examples 16, 19, 20, 21, 22(a), 22(c), 23, 24, 25, 29 and 30.

Synthesis Procedure (A')

A MOF synthesised according to procedure (A) is dried and then heated in water with stirring. The resulting MOF is then coiled, filtered and dried.

Example 28

10 g of the dried product from example 22(b) was heated in water at 70° C., with stirring, for 12 hr before being cooled, filtered and dried.

Figure 25:
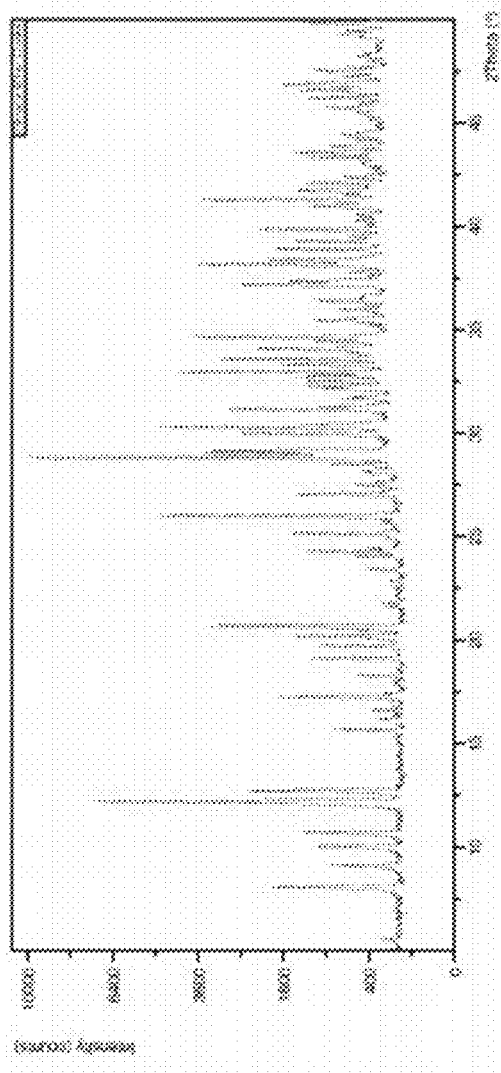
FIG. 25 shows an powder XRD pattern of the Ag-BTC MOF prepared according to example 28.
Figure 26A:
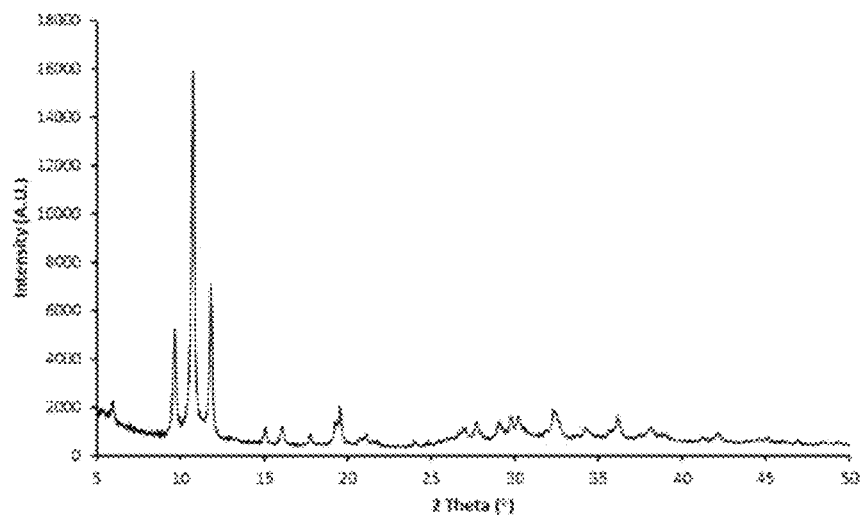
FIGS. 26(a) and (b) show powder XRD patterns of the Ag-BTC MOF prepared according to examples 29 and 30, respectively.
Figure 26B:
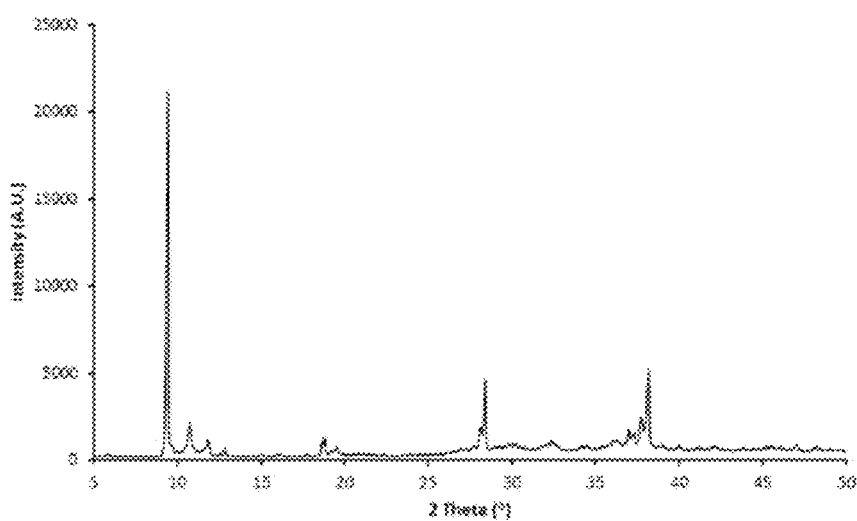

Approximate product composition of material synthesised in this manner was found to be in the range $Ag_{2-4}(BTC)_{0.5-2} \cdot 1\text{-}2H_2O$ (as determined from single crystal XRD and TGA studies). Powder XRD data (FIG. 25) and single crystal XRD data indicate that the material is a new phase and differs from the materials synthesised in examples 22(a)-(c).

Synthesis Procedure (B)

A suspension of trimesic acid in water (preferably distilled or deionised) is neutralised with base (for example, but not limited to, sodium hydroxide) until the desired pH is sufficiently high for the trimesic acid to dissolve. Once the acid has dissolved, the water is evaporated to leave a trimesate salt residue, which is purified by refluxing in a suitable solvent (e.g. ethanol). The salt is then recovered by an appropriate means such as filtration.

An aqueous solution of the trimesate salt is then prepared and a solution of a metal salt in an appropriate solvent (e.g. silver nitrate in water) is added, as described above in relation to method A, and the resulting MOF recovered and washed with water and ethanol. Example 26 of preparing a Ag-BTC MOF by method (B) is set out below.

Example 29

3.5 equiv of sodium hydroxide was added to a suspension of 1 equiv trimesic acid in distilled water with stirring. The trimesic acid slowly dissolved and the solution stirred for a further 30 minutes and the water evaporated. The residue was refluxed in ethanol for 30 minutes and recovered by filtration and air dried.

A solution of silver nitrate (3 equivalents) in distilled water was added dropwise to an aqueous solution of the sodium salt of trimesic acid with stirring. The product was recovered by filtration, washed with distilled water, then ethanol and air dried.

Synthesis Procedure (C)

A single crystal Ag-BTC MOF sample was prepared as follows:

Example 30

A solution of the sodium salt of trimesic acid (69.0 mg, 0.2 mmol) in distilled water (5 ml) was placed into the bottom of a test tube, to which distilled water (5 ml) was carefully layered on top and then a solution of silver nitrate (102.0 mg, 0.6 mmol, 3 equiv.) in distilled water (5 mL). The resultant layered solution was placed in the dark to crystallise for 4 days. The product was recovered by filtration, washed with distilled water, then ethanol and air dried. Small single crystals were visible.

Experimental

Powder X-Ray Diffraction

Data were collected on a Panalytical Empyrean diffractometer operating Cu K$\alpha_1$ radiation monochromated with a curved Ge (111) crystal in reflectance mode.

Single Crystal X-Ray Diffraction

Data were collected on beamline 11.3.1 at the Advanced Light Source, Berkeley, Calif. The structure was solved by direct methods (SHELXS97) and refined by full-matrix least-squares analysis (SHELXL-97).

Thermal Analysis

Data were collected on a TA Instruments SDT 2960. Samples were heated in an alumina crucible at a rate of 10° C. min$^{-1}$ to a maximum temperature of 900° C. in a flowing atmosphere of air.

Elemental Analysis

Data were collected on a Carlo Erba Flash 2000 Organic Elemental Analyser.

Antimicrobial Susceptibility

Antimicrobial susceptibility testing to determine the growth inhibition by the test items was carried out using modifications of the following Clinical and Laboratory Standards Institute (CLSI) Approved Standards:

Methods for Dilution Antimicrobial Susceptibility Tests for Bacteria that Grow Aerobically (M07-A8)

Antimicrobial susceptibility testing using the above CLSI Approved Standards requires test antimicrobial materials to be in an aqueous solution. As MOFs are solid disks it was not possible to follow these methods precisely. The MOFs were not optically transparent and therefore did not permit kinetic analysis of microbial growth by changes in optical density. Therefore, the above CLSI protocol was adapted to monitor microbial metabolic activity using 10% (v/v) resazurin (Alamar blue; a cell viability indicator) which detected growth by changes in fluorescence rather than optical density. Changes in fluorescence were determined using a BioTek Synergy HT Multi-Mode Microplate Reader.

The following bacterial strains were tested to determine antibacterial activity

*E. coli* NCTC9001
*P. mirabilis* NCTC11938
*S. aureus* DSMZ11729
*P. aeruginosa* Pa01
*P. aeruginosa* Pa058

Analytical Data

Powder X-Ray Diffraction

Powder X-ray diffraction data (FIGS. 20-26) show that the Ag-BTC materials made by the procedures A-C are new phases which differ (discussed above) from Ag_BTC MOFs described in the literature. In addition, there are no similar materials present within the International Centre for Diffraction Data, Powder Diffraction File ("ICDD PDF") database. These data also confirm that the materials prepared by the different synthesis methods of procedures A-C contain the same phases.

Example 22a was prepared at an elevated temperature of 60° C. The contrast of the corresponding powder XRD pattern (FIG. 22(a) to the patters shown in FIG. 20, for example, demonstrate the temperature sensitivity of the synthesis. This is further demonstrated by the differences between each of examples 22(a)-(c).

The powder diffraction pattern of example 30 differs from that of the previous examples by the addition of intense diffractions peaks (quantity in brackets) at approximately 9.4, 12.3, 18.6 (2), 28.2 (2), 36.8 (multiple) and 37.6 (2) ° 2θ. These peaks result from an impurity phase. Peaks common to samples 16-26 are also present.

Single Crystal X-Ray Diffraction

The material of example 27 was found to crystallise in the triclinic space group P-1, details of the crystal structure and refinement information are presented in Table 1.

TABLE 1

| Crystal data and structure refinement for AgBTC. | |
|---|---|
| Identification code | AgBTC |
| Empirical formula | $Ag_{14}(C_9H_3O_6)_4(OH)_2$ |
| Formula weight | 2372.65 |
| Temperature | 150(2) K |
| Wavelength | 0.77490 Å |
| Crystal system, space group | Triclinic, P-1 |
| Unit cell dimensions | a = 8.707(2) Å    α = 102.559(4) ° |
|  | b = 13.950(3) Å   β = 99.157(3) ° |
|  | c = 19.756(5) Å   γ = 100.934(4) ° |
| Volume | 2249.0(9) Å$^3$ |
| Z, Calculated density | 2, 3.504 Mg/m$^3$ |
| Absorption coefficient | 6.039 mm$^{-1}$ |
| F(000) | 2192 |
| Crystal size | 0.01 × 0.01 × 0.05 mm |
| Theta range for data collection | 2.79 to 34.57° |

TABLE 1-continued

Crystal data and structure refinement for AgBTC.

| Limiting indices | $-12 <= h <= 12, -20 <= k <= 19,$ |
| --- | --- |
|  | $-28 <= l <= 28$ |
| Reflections collected/unique | 32843/13747 [R(int) = 0.0685] |
| Completeness to theta = 34.57 | 92.90% |
| Refinement method | Full-matrix least-squares on $F^2$ |
| Data/restraints/parameters | 13747/140/365 |
| Goodness-of-fit on $F^2$ | 1.166 |
| Final R indices [I > 2 sigma(I)] | $R_1 = 0.2468, wR_2 = 0.5677$ |
| R indices(all data) | $R_1 = 0.2916, wR_2 = 0.5854$ |
| Largest diff. peak and hole | 9.820 and $-22.325$ e · Å$^{-3}$ |

Figure 27:
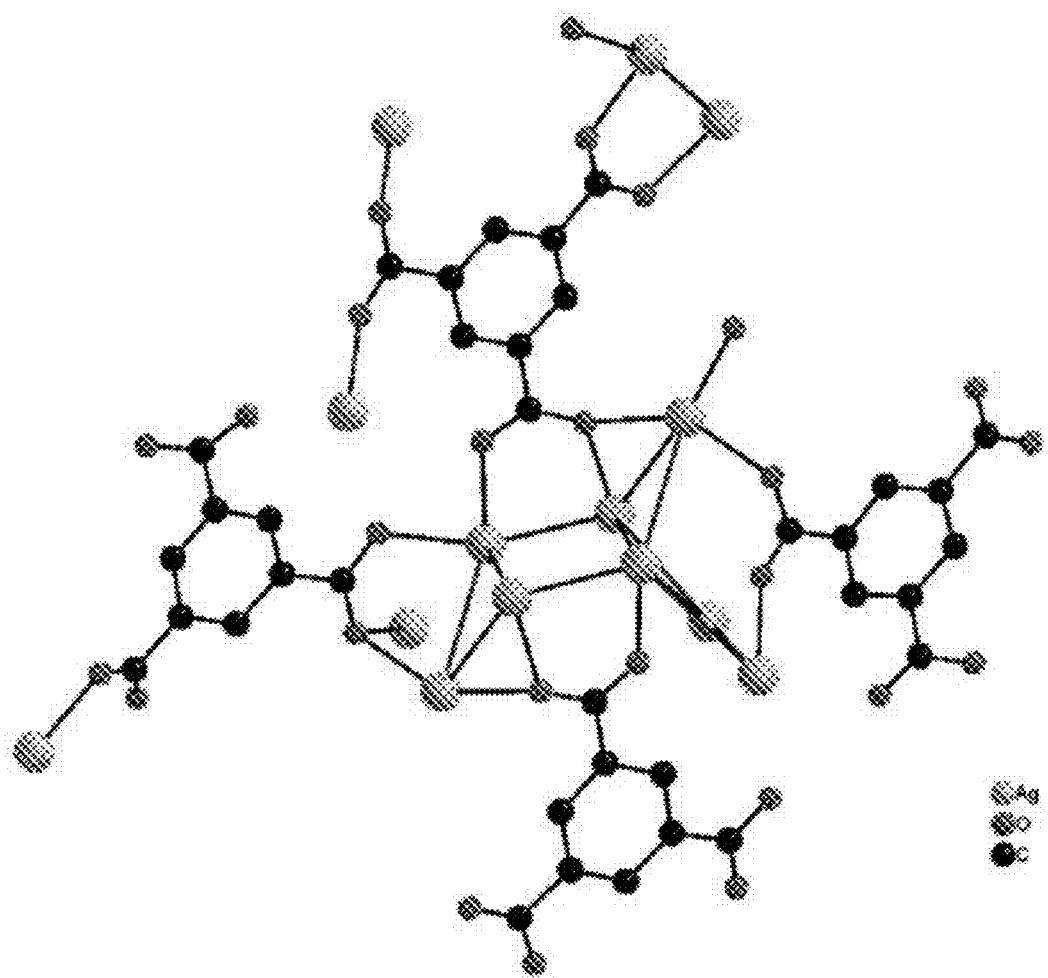
FIG. 27 shows the asymmetric unit cell of the Ag-BTC MOF.
Figure 28:
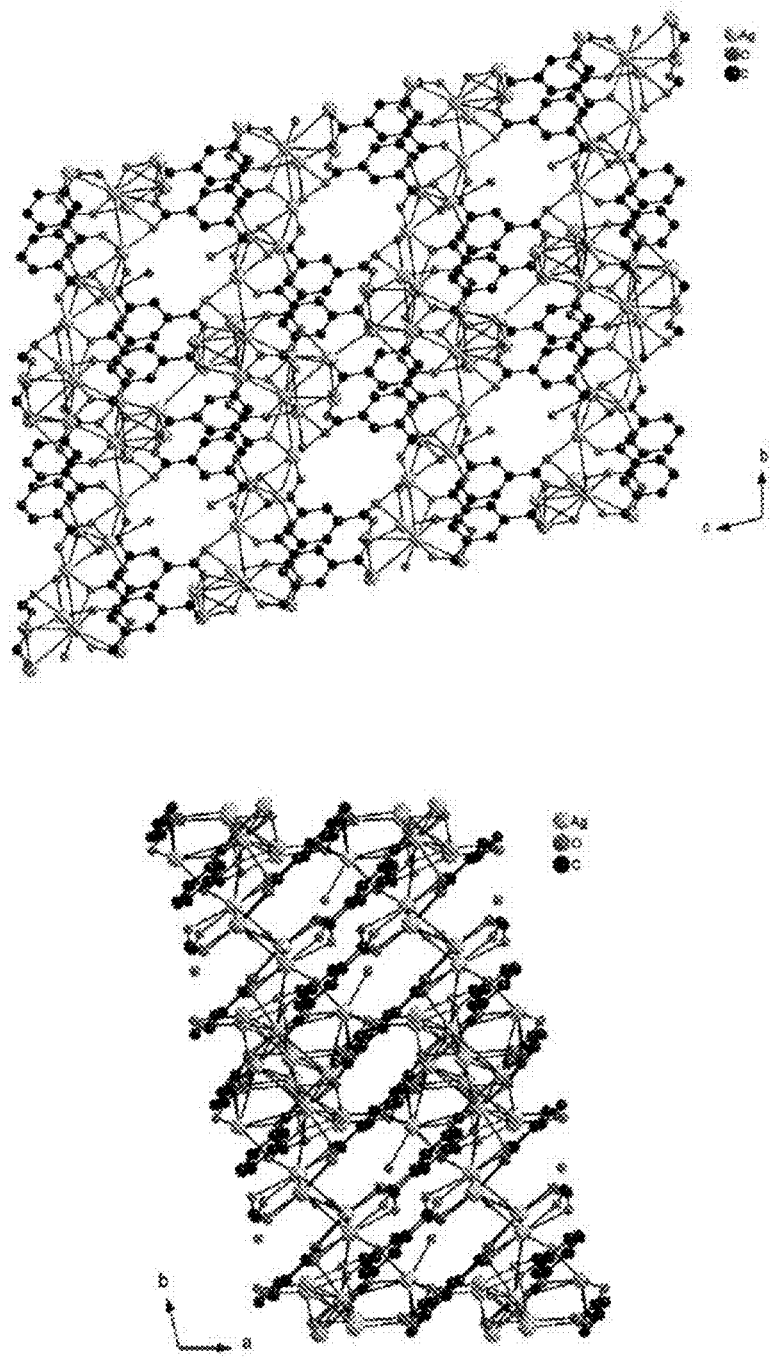
FIG. 28 shows a ball and stick representation of the Ag-BTC along the a-(top) and c-axis (bottom), respectively.

FIG. 27 shows the asymmetric unit contains fourteen silver (I) ions, four molecules of trimesate and two hydroxyls to give an overall chemical formula of $Ag_{14}(C_9H_3O_6)_4(OH)_2$. This produces a three-dimensional connected material with small pores along the a-axis that contain protruding hydroxyl groups (FIG. 28).

Chemical Composition

TABLE 2

Results of CHN elemental analysis.

| | C (wt %) | | H (wt %) | | N (wt %) | |
| --- | --- | --- | --- | --- | --- | --- |
| | (1) | (2) | (1) | (2) | (1) | (2) |
| Example 1 | 18.83 | 18.97 | 1.25 | 1.17 | <0.1 | <0.1 |
| Example 2 | 19.32 | 19.19 | 1.07 | 1.16 | <0.1 | <0.1 |
| Example 3 | 18.95 | 19.05 | 1.08 | 1.14 | <0.1 | <0.1 |
| Theoretical | 18.22 | | 0.59 | | 0.00 | |

Figure 29:
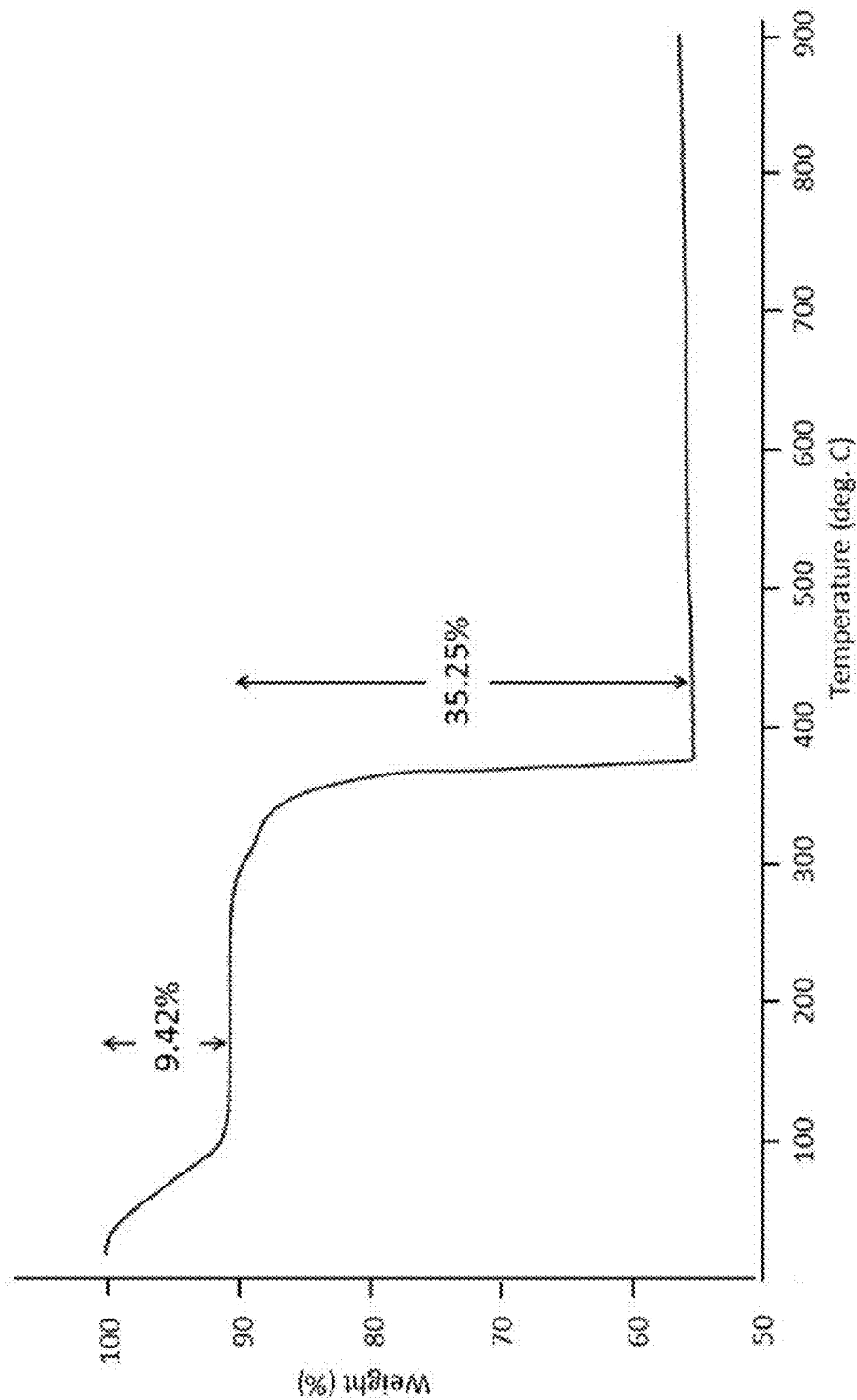
FIG. 29 shows the thermogravimetric analysis of the Ag-BTC of example 16.
Figure 30:
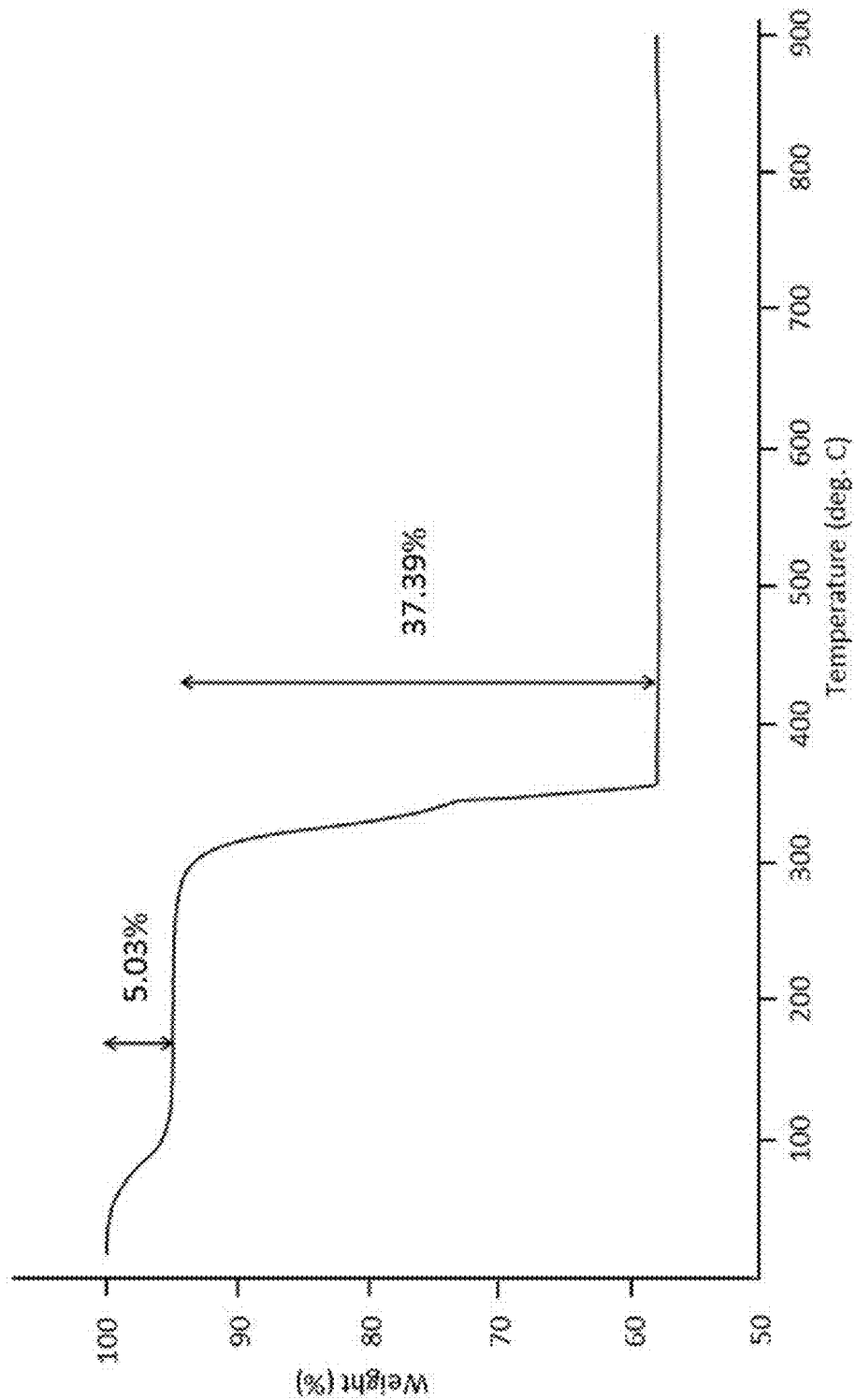
FIG. 30 shows the thermogravimetric analysis of the Ag-BTC of example 29.
Figure 31:
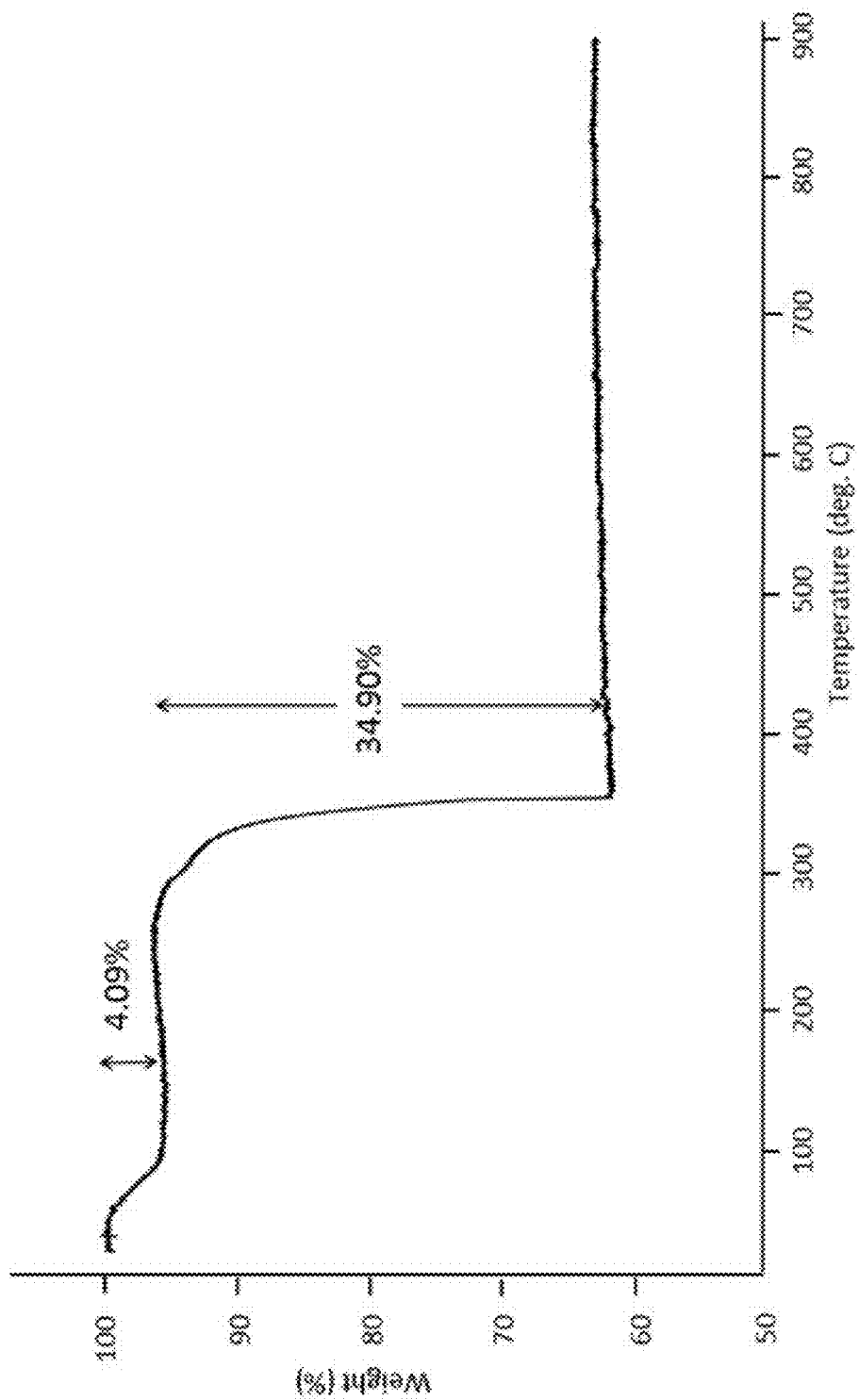
FIG. 31 shows the thermogravimetric analysis of the Ag-BTC of example 30.

The refined structure obtained from single crystal X-ray diffraction is also consistent with the results obtained from the CHN elemental analysis (Table 2). However, there are differences in the thermogravimetic analysis (TGA), FIGS. 29-31, which explain the small discrepancies from the CHN elemental analysis. The TGA data infer that there are volatiles present within the small pores of the material (water or ethanol from the synthesis method) and this could be contributing to the differences observed in both the TGA and elemental analysis.

Thermal analysis revealed a mass loss between ambient to ~120° C. ranging from 4.09-9.42 wt % and a further mass loss between 120° C. and 400° C. ranging from 34.90-37.39 wt %. The first mass loss is attributed to volatiles (water and/or ethanol) and the second to trimesate with a solid residue ranging from 55.39-61.72 wt %. The discrepancies could be due to the different synthetic routes and therefore represents a window of chemical composition for this novel material.

Microbial Susceptibility Testing

E. coli (NCTC9001).

Figure 32:
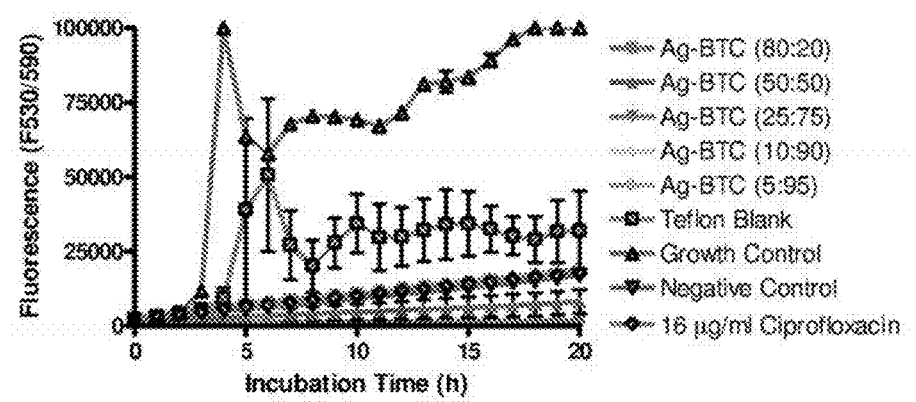
FIG. 32 shows growth inhibition of *E. coli* NCTC9001.
Figure 33:
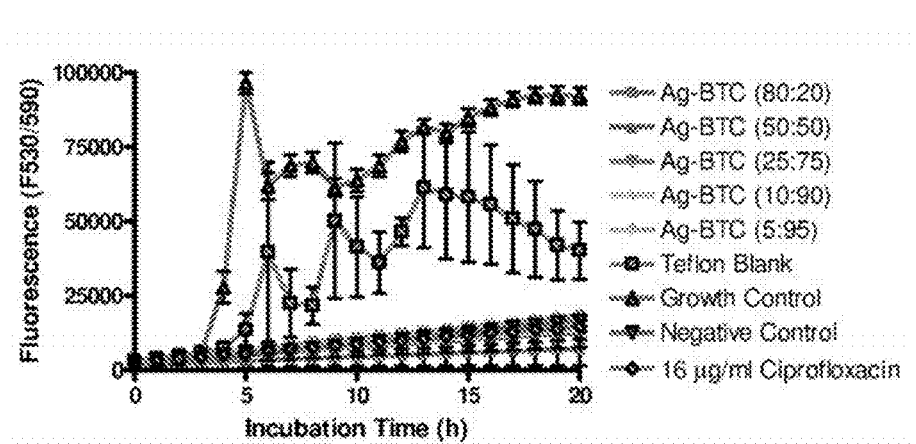
FIG. 33 shows growth inhibition of *P. mirabilis* NCTC11938.

The results in FIG. 32 demonstrate that the above material inhibits metabolic activity of E. coli (NCTC9001) after 20 hours incubation at 37° C. under aerobic conditions.

P. mirabilis (NCTC11938).

Figure 14:
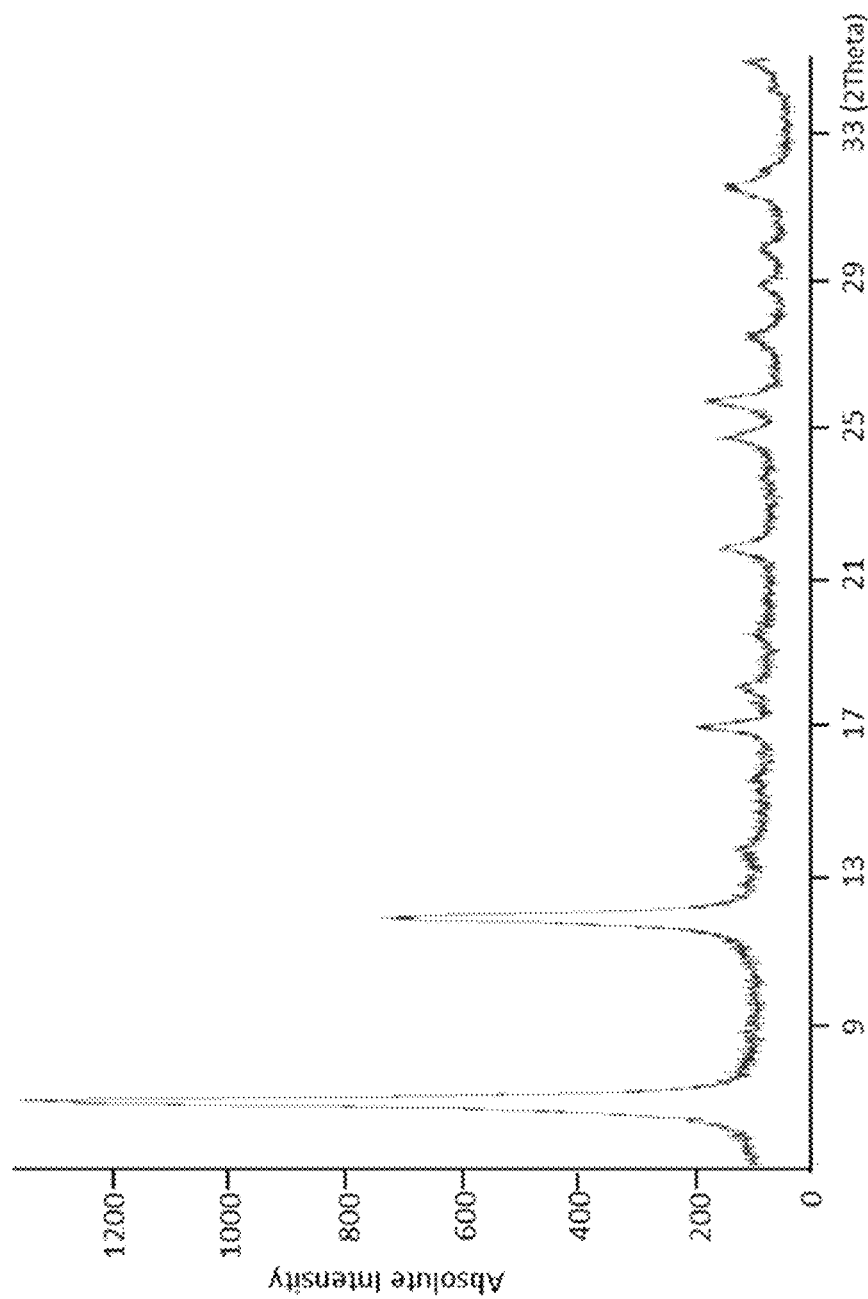
FIG. 14 shows XRD patterns for $Zn_xNa_z(dhtp)(H_2O)_g \cdot hH_2O$ prepared as per example 6.
Figure 15:
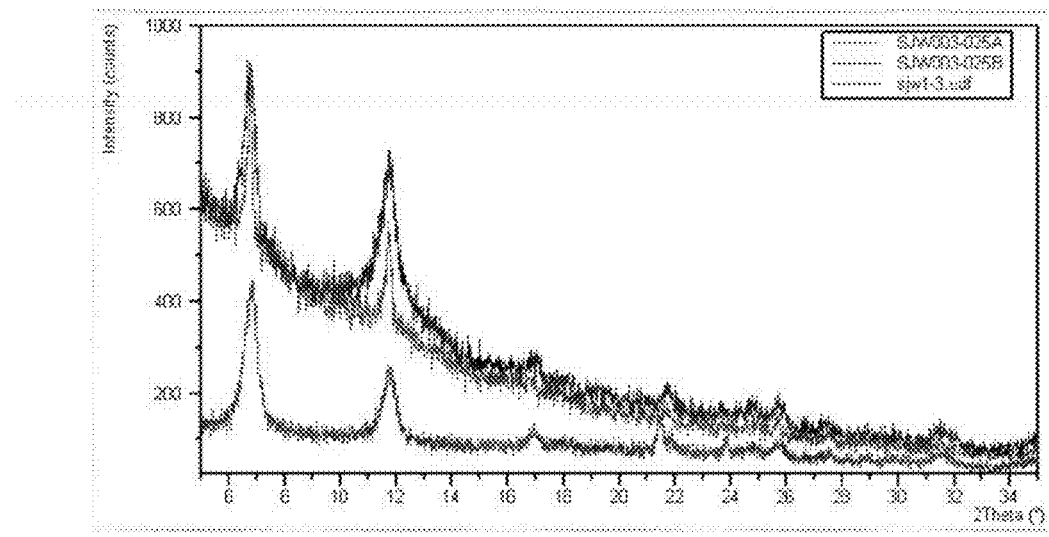
FIG. 15 shows XRD patterns for $Zn_xNa_z(dhtp)(H_2O)_g \cdot hH_2O$ prepared as per example 7 (blue), 8 (red) and 3a (dark blue)
Figure 16:
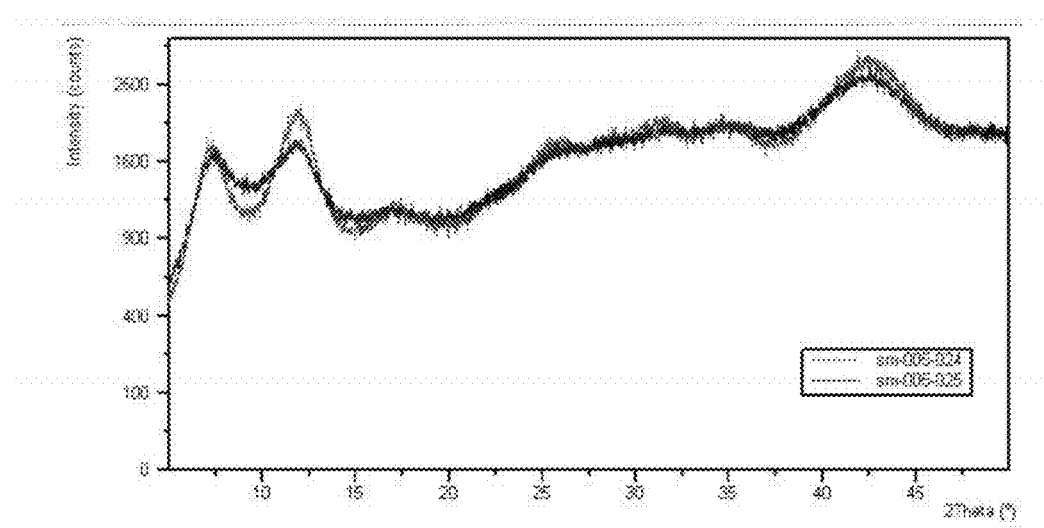
FIG. 16 shows XRD patterns for $Ni_yNa_z(dhtp)(H_2O)_g \cdot hH2O$ synthesised as per Example 9. Red: order of addition: water, ethanol, Ni acetate, NaDHTP. Blue: order of addition—water, Ni acetate, NaDHTP, ethanol.
Figure 17A:
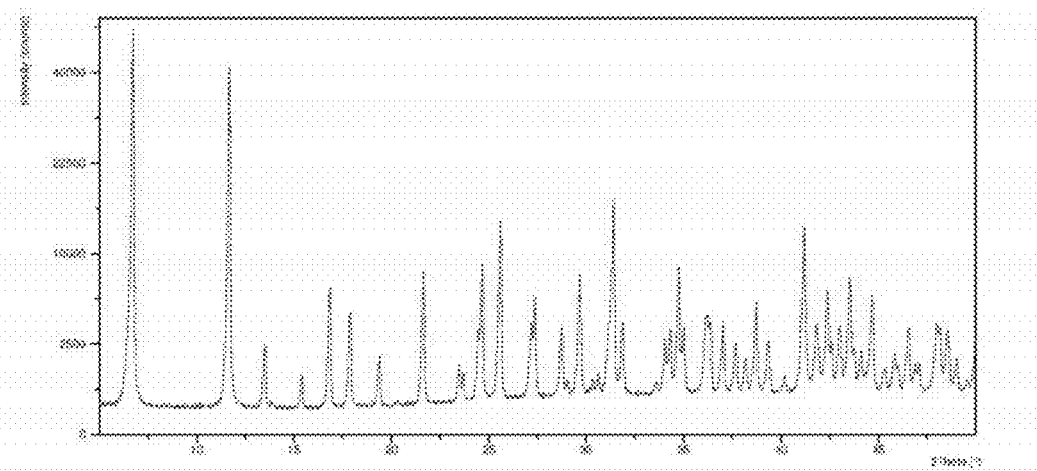
FIG. 17a shows XRD pattern of ZnNaDHTP prepared as per example 11b.
Figure 17B:
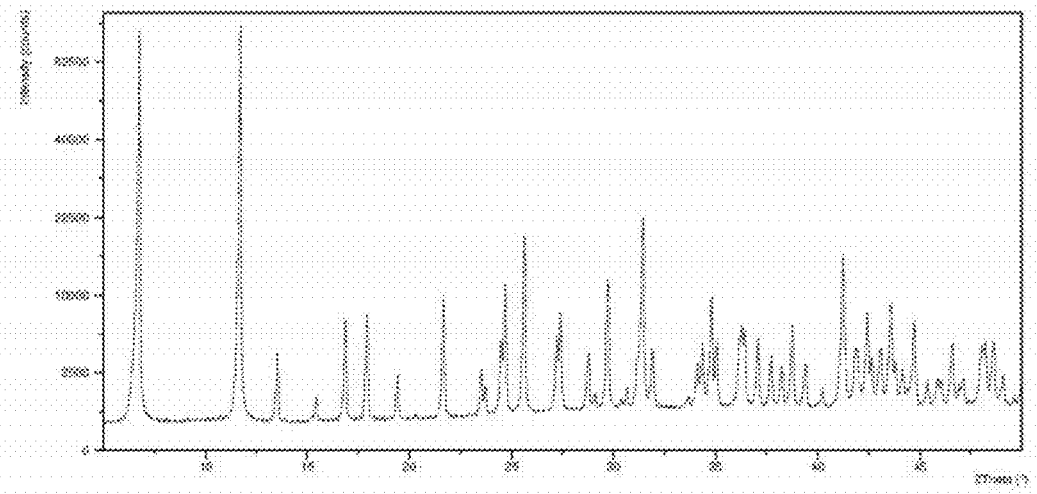
FIG. 17b shows XRD pattern of ZnNaDHTP prepared as per example 13.
Figure 18:
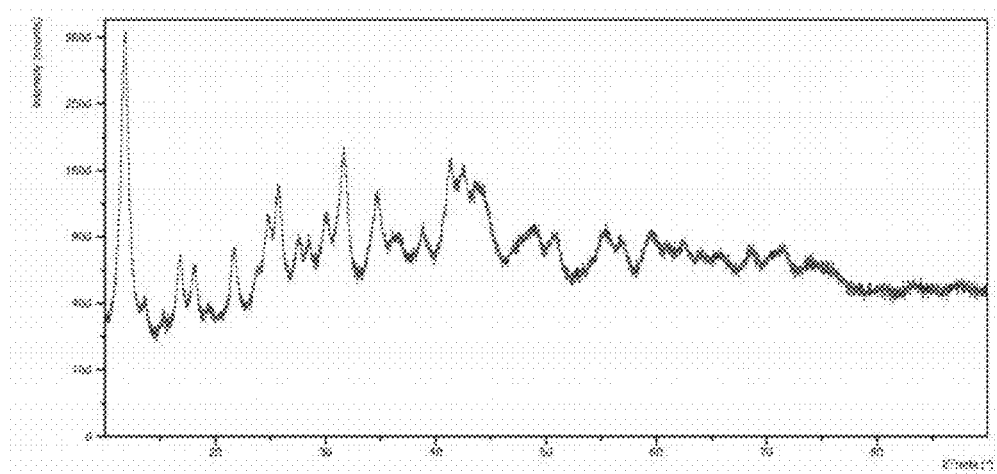
FIG. 18 shows XRD pattern of NiNaDHTP prepared as per example 4c.
Figure 19:
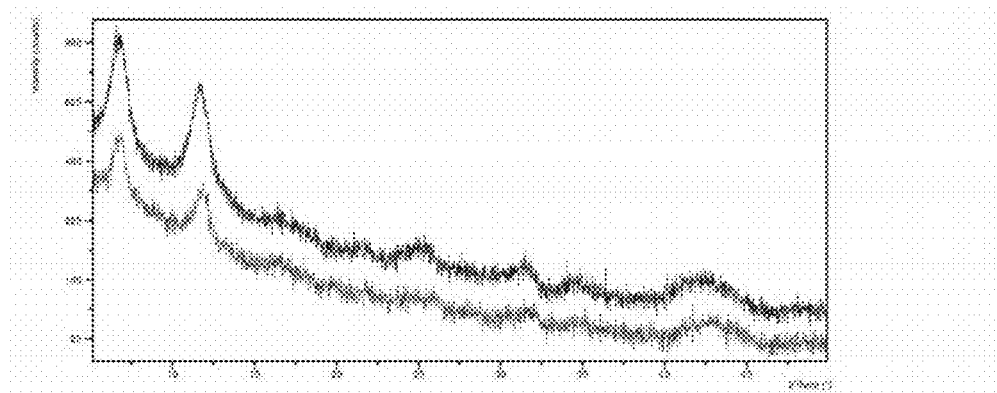
FIG. 19 shows XRD patterns of NiNaDHTP prepared as per example 15a (bottom) and 15b (top)
Figure 20:
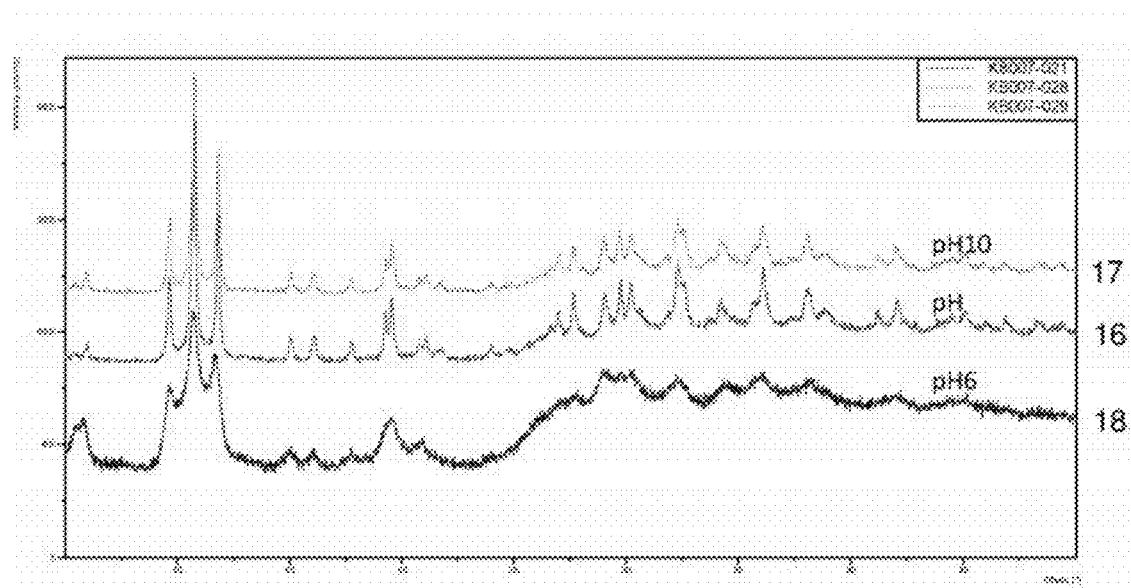
FIG. 20 shows powder XRD patterns of the Ag-BTC MOF prepared according to examples 16 (middle), 17 (top) and 18 (bottom).
Figure 21:
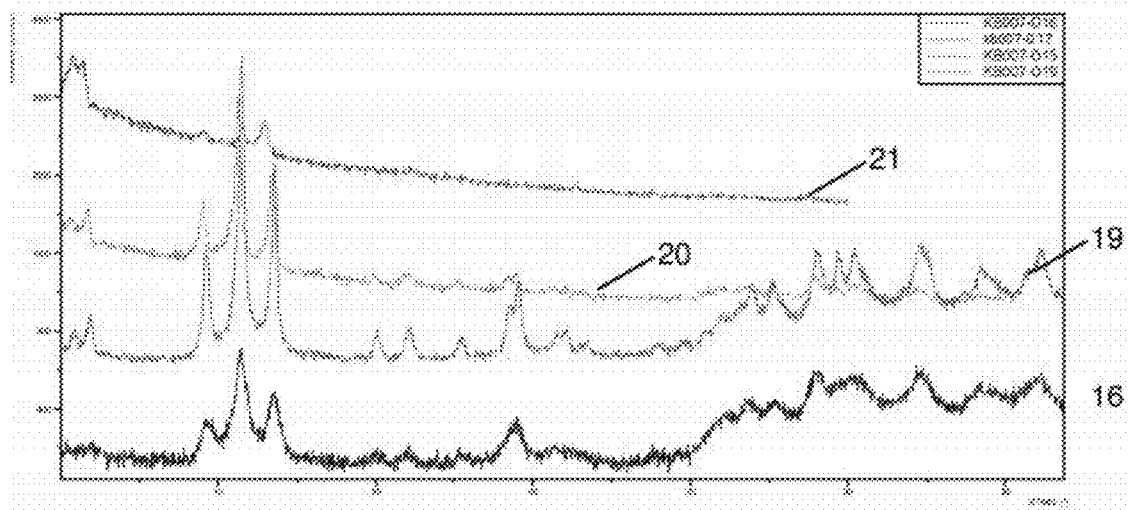
FIG. 21 shows powder XRD patterns of the Ag-BTC MOF prepared according to examples 16, 19, 20 and 21 (bottom to top).

The results in FIG. 14 demonstrate that the above material inhibits the metabolic activity of P. mirabilis (NCTC11938) after 20 hours incubation at 37° C. under aerobic conditions.

P. aeruginosa (Pa01).

Figure 34:
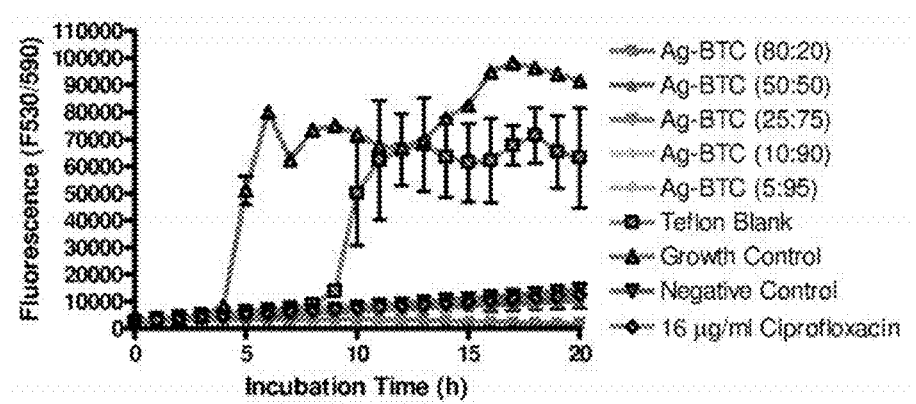
FIG. 34 shows growth inhibition of *P. aeruginosa* (Pa01).

The results in FIG. 34 demonstrate that the above material inhibits the metabolic activity of P. aeruginosa (Pa01) after 20 hours incubation at 37° C. under aerobic conditions.

P. aeruginosa (Pa058).

Figure 35:
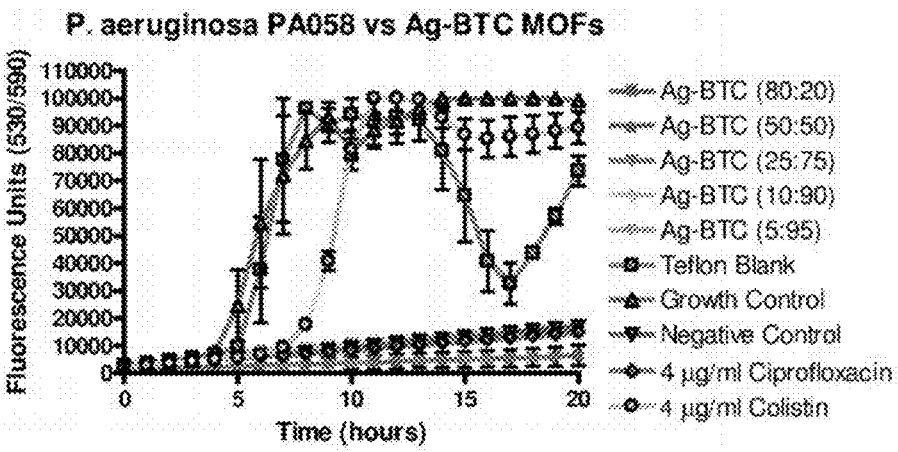
FIG. 35 shows growth inhibition of *P. aeruginosa* (Pa058).

The results in FIG. 35 demonstrate that the above material inhibits the metabolic activity of P. aeruginosa (Pa058) after 20 hours incubation at 37° C. under aerobic conditions.

S. aureus (DSMZ11729).

Figure 36:
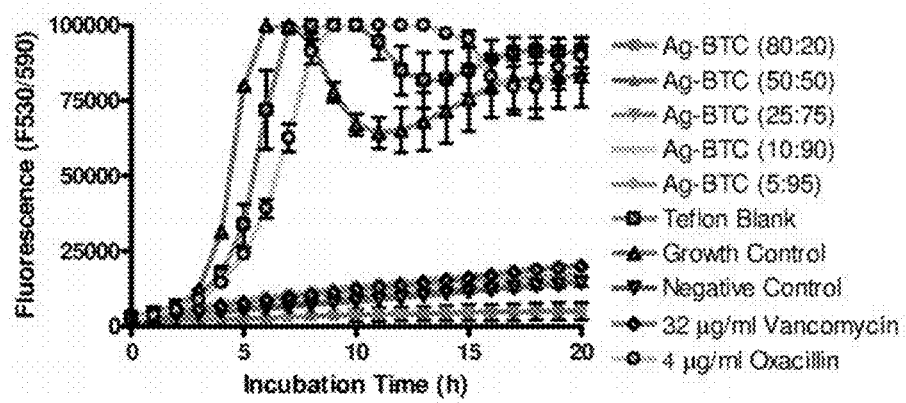
FIG. 36 shows growth inhibition of *S. aureus* (DSMZ11729).

The results in FIG. 36 demonstrate that the above material inhibits the metabolic activity of S. aureus (DSMZ11729) after 20 hours incubation at 37° C. under aerobic conditions.

These data show that the novel silver trimesate MOF material of the present invention shows excellent antibacterial activity towards several strains of bacterium. It is proposed that the antibacterial properties may be related to the comparatively high silver content (in relation to previously reported Ag-MOFs).

REFERENCES

1. R. E. Morris and P. S. Wheatley, Angew. Chem. Int. Ed., 2008, 47, 4966
2. A. C. McKinlay, B. Xiao, D. S. Wragg, P. S. Wheatley, I. L. Megson and R. E. Morris, J. Am. Chem. Soc., 2008, 130, 10440
3. P. D. C. Dietzel, B. Panella, M. Hirscher, R. Blom and H. Fjellveg, Chem. Comm., 2006, 959
4. P. D. C. Dietzel, R. E. Johnsen, R. Blom and H. Fjellveg, Chem. Eur. J. 2008, 14, 2389
5. N. L. Rosi, J. Kim, M. Eddaoudi, B. Chen, M. O'Keeffe and O. M. Yaghi, J. Am. Chem. Soc, 2005, 127, 1504
6. P. K. Allan, P. S. Wheatley, D. Aldous, M. I. Mohideen, C. Tang, J. A. Hriljac, I. L. Megson, K. W. Chapman, G. de Weireld, S. Vaesen, R. E. Morris, Dalton Transactions, 2012 in press R. Morris, P. S. Wheatley, Patent application WO 2008/020218 A1
8. Z. Bao, S. Alnemrat, L. Yu, I. Vasiliev, Q. Ren, X. Lu and S. Deng, Langmuir, 2011, 27, 13554
9. J. A. Botas, G. Calleja, M. Sanchez-Sanchez and M. G. Orcajo, Int. J. of Hydrogen Energ, 2001, 36, 10834
10. D. J. Tranchemontagne, J. R. Hunt and O. M. Yaghi, Tetrahedron, 2008, 64, 8553
11. H. Du, J. Bai, C. Zuo, Z. Xin and J. Hu, Cryst. Eng. Comm., 2011, 13, 3314
12. N. E. Ghermani, G. Morgant, J. d'Angelo, D. Desmaele, B. Fraisse, F. Bonhomme, E. Dichi and M. Sgahier, Polyhedron, 2007, 26, 2880.

The invention claimed is:

1. A metal organic framework of the form $M_{x'}(BTC)_{y'}(OH)_{y'}(H_2O)_{w'}$, where M is Ag, BTC is 1,3,5-benzene tricarboxylate, x' has a value in a range from 1-5, y' has a value in a range from 0.1 to 3, v' has a value in a range from 0 to 2 and w' has a value in a range from 0-5.

2. The metal organic framework according to claim 1, wherein x' is in a range from 2-4 and y' is in a range from 0.5 to 2.

3. The metal organic framework according to claim 1, wherein x' is 3-4, y' is 0.8 to 1.2, v' is 0 to 1 and w' is 0-5.

4. The metal organic framework according to claim 1, obtained or obtainable by a method comprising adding together a suspension of trimesic acid and a basic solution, to thereby provide an aqueous solution of a salt of 1,3,5-benzene tricarboxylate.

5. The metal organic framework according to claim 1, obtained or obtainable by mixing an aqueous solution of a salt of 1,3,5-benzene tricarboxylate with an aqueous solution of silver nitrate.

6. An antimicrobial formulation comprising the metal organic framework of claim 1 and one or more additives.

* * * * *